United States Patent
Yamada et al.

(10) Patent No.: US 9,574,045 B2
(45) Date of Patent: Feb. 21, 2017

(54) EPOXY RESIN COMPOSITION, EPOXY RESIN, AND CURED PRODUCT

(71) Applicant: ASAHI KASEI E-MATERIALS CORPORATION, Tokyo (JP)

(72) Inventors: Teruhisa Yamada, Tokyo (JP); Kenzo Onizuka, Tokyo (JP); Kozo Yoshida, Tokyo (JP); Seiji Yamaguchi, Tokyo (JP)

(73) Assignee: ASAHI KASEI E-MATERIALS CORPORATION, Tokyo (JP)

( * ) Notice: Subject to any disclaimer, the term of this patent is extended or adjusted under 35 U.S.C. 154(b) by 0 days.

(21) Appl. No.: 14/416,605

(22) PCT Filed: Jul. 31, 2013

(86) PCT No.: PCT/JP2013/070774
§ 371 (c)(1),
(2) Date: Jan. 22, 2015

(87) PCT Pub. No.: WO2014/021386
PCT Pub. Date: Feb. 6, 2014

(65) Prior Publication Data
US 2015/0183924 A1 Jul. 2, 2015

(30) Foreign Application Priority Data

Jul. 31, 2012 (JP) .................................. 2012-170493
Aug. 23, 2012 (JP) .................................. 2012-184476

(51) Int. Cl.
*C08L 63/00* (2006.01)
*H01L 23/58* (2006.01)
(Continued)

(52) U.S. Cl.
CPC ............ *C08G 59/38* (2013.01); *C07D 303/28* (2013.01); *C08G 59/24* (2013.01); *C08G 59/245* (2013.01); *C08L 63/00* (2013.01)

(58) Field of Classification Search
CPC ......... C08G 59/38; C08G 59/24; C08L 63/00; C07D 303/28
(Continued)

(56) References Cited

U.S. PATENT DOCUMENTS

2002/0061941 A1  5/2002  Masamune et al.
2013/0144015 A1* 6/2013  Hefner ................... C08G 59/24
                                                        525/524
2014/0163180 A1* 6/2014  Hefner, Jr. ............. C08G 59/04
                                                        525/524

FOREIGN PATENT DOCUMENTS

JP       36-20393       10/1961
JP       1-275621 A     11/1989
(Continued)

OTHER PUBLICATIONS

English translation of International Search Report issued Oct. 22, 2013, in PCT International Application No. PCT/JP2013/070774.
(Continued)

*Primary Examiner* — David Karst
(74) *Attorney, Agent, or Firm* — Birch, Stewart, Kolasch & Birch, LLP

(57) ABSTRACT

The present invention provides an epoxy resin composition including an epoxy resin represented by the following formula (1) and an epoxy resin represented by the following formula (2):

(1)

(Continued)

-continued

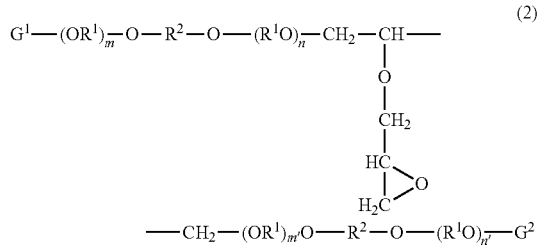

(2)

9 Claims, 3 Drawing Sheets

(51) Int. Cl.
*C08G 59/38* (2006.01)
*C08G 59/24* (2006.01)
*C07D 303/28* (2006.01)

(58) Field of Classification Search
USPC .......... 525/103, 524, 534; 528/103; 257/798
See application file for complete search history.

(56) References Cited

FOREIGN PATENT DOCUMENTS

| | | | |
|---|---|---|---|
| JP | 8-333357 | A | 12/1996 |
| JP | 10-77330 | A | 3/1998 |
| JP | 2001-302759 | A | 10/2001 |
| JP | 2003-201334 | A | 7/2003 |
| JP | 2003-246837 | A | 9/2003 |
| JP | 2004-83839 | A | 3/2004 |
| JP | 2009-203425 | A | 9/2009 |
| TW | I239980 | B | 9/2005 |

OTHER PUBLICATIONS

International Preliminary Report on Patentability and English translation of Written Opinion issued Feb. 3, 2015, in PCT International Application No. PCT/JP2013/070774.
Supplementary European Search Report issued Jun. 16, 2015, in European Patent Application No. 13825198.8.

* cited by examiner

EPOXY RESIN COMPOSITION, EPOXY RESIN, AND CURED PRODUCT

TECHNICAL FIELD

The present invention relates to an epoxy resin composition, an epoxy resin and a cured product.

BACKGROUND ART

The cured products of epoxy resin compositions each including an epoxy resin and a curing agent are used in various applications including, for example, electronic parts of semiconductor packages and semiconductor chips. For example, Patent Literature 1 discloses a method for producing an epoxy resin having a polyether group in which the number of the repeating units formed of an alkyleneoxy group is less than three. Patent Literature 2 discloses a method for producing an epoxy resin having a polyether group in which the number of the repeating units formed of an alkyleneoxy group is less than six.

CITATION LIST

Patent Literature

Patent Literature 1: Japanese Patent Publication No. 36-020393
Patent Literature 2: Japanese Patent Laid-Open No. 2003-246837

SUMMARY OF INVENTION

Technical Problem

Recently, semiconductor packages and semiconductor chips have been strongly required to be smaller in size and thinner in thickness. Accordingly, epoxy resins used as the materials for these packages and tips are demanded to be low in viscosity and excellent in adhesiveness, and to yield cured products thereof excellent in flexibility. Moreover, the foregoing epoxy resins are also demanded to be low in the contents of halogen-containing impurities (so-called, low-halogen epoxy resins) from the viewpoint of corrosion resistance and electric reliability. However, conventional epoxy resins cannot sufficiently meet such demands to leave room for further development of epoxy resins.

For example, the cured product of an epoxy resin disclosed in Patent Literature 1 cannot attain sufficient flexibility. The cured product of an epoxy resin disclosed in Patent Literature 2 cannot attain sufficient flexibility and poor in adhesiveness. Moreover, the epoxy resin is small in the content proportion of the epoxy groups at both terminals and hence is poor in reactivity. Yet moreover, the epoxy resin is high in viscosity and poor in compatibility with other epoxy resins.

The present invention has been achieved in view of the above-described circumstances, and an object of the present invention is to provide an epoxy resin composition and an epoxy resin, being low in viscosity, but being capable of yielding a cured product excellent in flexibility, adhesiveness and low water absorbency.

Solution to Problem

The present inventors made a diligent study, and consequently have perfected the present invention by discovering that the above-described problems can be solved by using an epoxy resin composition or an epoxy resin having the following constitution.

Specifically, the present invention is as follows.

[1]
An epoxy resin composition including:
an epoxy resin represented by the following formula (1); and
an epoxy resin represented by the following formula (2):

[Formula 1]

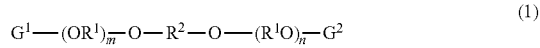

[Formula 2]

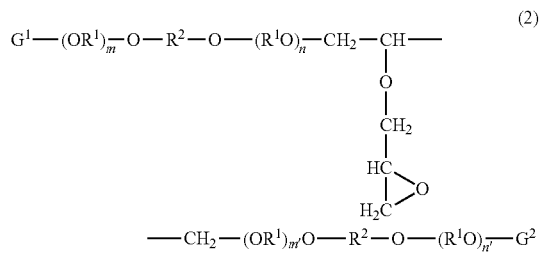

wherein m, n, m' and n' are each independently an integer of 1 to 30, $R^1$ and $R^2$ each independently represent a divalent aliphatic group having 1 to 12 carbon atoms or a divalent aromatic group having 6 to 40 carbon atoms, at least one of $R^1$ and $R^2$ represents a divalent aromatic group having 6 to 30 carbon atoms, $G^1$ represents a glycidyl group, and $G^2$ represents a hydrogen atom or a glycidyl group.

[2]
The epoxy resin composition according to [1], including:
100 parts by mass of the epoxy resin represented by formula (1); and
0.1 to 10 parts by mass of the epoxy resin represented by formula (2).

[3]
The epoxy resin composition according to [1] or [2], wherein $R^2$ in the formula (1) is any one selected from the group consisting of a phenylene group, a naphthylene group, a biphenylene group and a divalent aromatic group having structure represented by the following formula (3a):

[Formula 3]

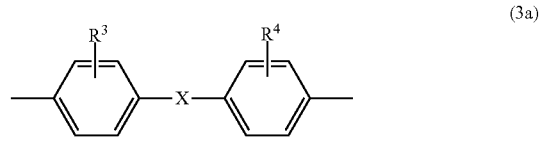

wherein $R^3$ and $R^4$ each independently represent any one selected from the group consisting of a hydrogen atom, a halogen atom, a hydroxyl group, an alkoxy group having 1 to 12 carbon atoms, a carboxyl group and an alkyl group having 1 to 12 carbon atoms, and X represents any one selected from the group consisting of an alkylene group having 1 to 10 carbon atoms, —O—, —CO—, —COO—, —S—, —SO—, —$SO_2$— and —S—S—.

[4]
The epoxy resin composition according to any one of [1] to [3], wherein at least one of $R^2$ in the formula (2) is any one selected from the group consisting of a phenylene group, a naphthylene group, a biphenylene group and a divalent aromatic group having the structure represented by the following formula (3b):

[Formula 4]

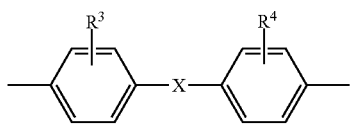
(3b)

wherein $R^3$ and $R^4$ each independently represent any one selected from the group consisting of a hydrogen atom, a halogen atom, a hydroxyl group, an alkoxy group having 1 to 12 carbon atoms, a carboxyl group and an alkyl group having 1 to 12 carbon atoms, and X represents any one selected from the group consisting of an alkylene group having 1 to 10 carbon atoms, —O—, —CO—, —COO—, —S—, —SO—, —SO$_2$— and —S—S—.

[5]
The epoxy resin composition according to any one of [1] to [4], wherein the formula (1) is represented by the following formula (4), and the formula (2) is represented by the following formula (5):

[Formula 5]

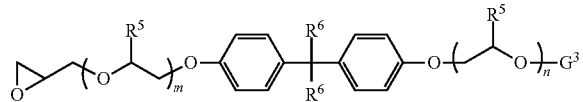
(4)

wherein $R^5$ and $R^6$ each independently represent a hydrogen atom or a methyl group, $G^3$ represents a hydrogen atom or a glycidyl group, and m and n are each independently an integer of 1 or more and satisfy a relation represented by $3 \leq (m+n) \leq 12$,

[Formula 6]

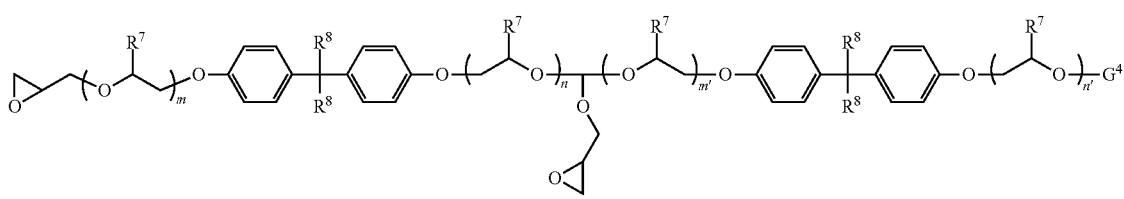
(5)

wherein $R^7$ and $R^8$ each independently represent a hydrogen atom or a methyl group, and $G^4$ represents a hydrogen atom or a glycidyl group; and m, n, m' and n' are each independently an integer of 1 or more, and satisfy a relation represented by $6 \leq (m+n+m'+n') \leq 20$.

[6]
The epoxy resin composition according to [5], wherein $G^4$ in the formula (5) is a glycidyl group.

[7]
An epoxy resin represented by the following formula (1),
wherein m and n in the formula (1) are each independently an integer of 1 to 11, and satisfy a relation represented by $3 \leq (m+n) \leq 12$; and
a proportion of the component having m and n satisfying a relation represented by $6 \leq (m+n) \leq 12$ in the epoxy resin is 30 mol % or more and 70 mol % or less.

[Formula 7]

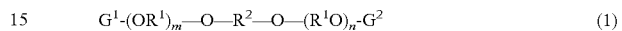

$G^1\text{-}(OR^1)_m\text{—}O\text{—}R^2\text{—}O\text{—}(R^1O)_n\text{-}G^2$ (1)

wherein m and n are each independently an integer of 1 to 30, $R^1$ and $R^2$ each independently represent an aliphatic group having 1 to 12 carbon atoms or a divalent aromatic group, at least one of $R^1$ and $R^2$ represents a divalent aromatic group having 6 to 30 carbon atoms, $G^1$ represents a glycidyl group, and $G^2$ represents a hydrogen atom or a glycidyl group.

[8]
The epoxy resin according to [7], wherein a proportion of a component represented by formula (1) with $G^2$ representing a glycidyl group in the epoxy resin is 10 mol % or more and 100 mol % or less.

[9]
The epoxy resin according to [7] or [8],
wherein $R^2$ in the formula (1) is any one selected from the group consisting of a phenylene group, a naphthylene group, a biphenylene group and a divalent aromatic group having the structure represented by the following formula (3a):

[Formula 8]

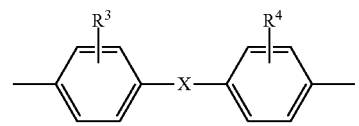
(3a)

wherein $R^3$ and $R^4$ each independently represent any one selected from the group consisting of a hydrogen atom, a halogen atom, a hydroxyl group, an alkoxy group having 1 to 12 carbon atoms, a carboxyl group and an alkyl group having 1 to 12 carbon atoms, and X represents any one selected from the group consisting of an alkylene group having 1 to 10 carbon atoms, —O—, —CO—, —COO—, —S—, —SO—, —SO$_2$— and —S—S—.

[10]

The epoxy resin according to any one of [7] to [9], wherein a total chlorine content is 1000 ppm by mass or less.

[11]

An epoxy resin composition including:

the epoxy resin composition according to any one of [1] to [6], or the epoxy resin according to any one of [7] to [10]; and a curing agent.

[12]

A cured product obtained by curing the epoxy resin composition according to [11].

[13]

A cured product obtained from the epoxy resin represented by the following formula (1), wherein when the cured product is subjected to a cured product measurement at a frequency of 1 Hz with a dynamic viscoelastic measurement apparatus, the cured product satisfies a relation represented by the following mathematical expression (a) and a relation represented by the following mathematical expression (b):

[Formula 9]

$$G^1\text{-}(OR^1)_m\text{—O—}R^2\text{—O—}(R^1O)_n\text{-}G^2 \quad (1)$$

wherein m and n are each independently an integer of 1 to 30, $R^1$ and $R^2$ each independently represent an aliphatic group having 1 to 12 carbon atoms or a divalent aromatic group, at least one of $R^1$ and $R^2$ represents a divalent aromatic group having 6 to 30 carbon atoms, $G^1$ represents a glycidyl group, and $G^2$ represents a hydrogen atom or a glycidyl group, $$E'/(273+T^1/3)<8.5 \quad (a)$$

wherein $T^1$ is a obtained peak top temperature of a loss tangent, and E'(MPa) is a storage modulus measured at 30° C., $$E'(T^1-20)>10\times E'(T^1+20) \quad (b)$$

wherein $E'(T^1-20)$ is a storage modulus measured at $(T^1-20)°$ C., and $E'(T^1+20)$ is a storage modulus measured at $(T^1+20)°$ C.

[14]

The cured product according to [13], wherein the cured product further satisfies a relation represented by the following mathematical expression (c), and a relation represented by the following mathematical expression (d):

$$E'/(273+T^1/3)<7 \quad (c)$$

wherein E' is the storage modulus measured at 30° C., and $T^1$ is the obtained peak top temperature of the loss tangent, $$E'(T^1-20)>20\times E'(T^1+20) \quad (d)$$

wherein E' is the storage modulus measured at 30° C., and $T^1$ is the obtained peak top temperature of the loss tangent.

[15]

An electronic part including the cured product according to any one of [12] to [14].

Advantageous Effects of Invention

According to the present invention, it is possible to provide an epoxy resin composition and an epoxy resin, being low in viscosity, but being capable of yielding a cured product excellent in flexibility, adhesiveness and low water absorbency.

DESCRIPTION OF EMBODIMENTS

Figure 1:
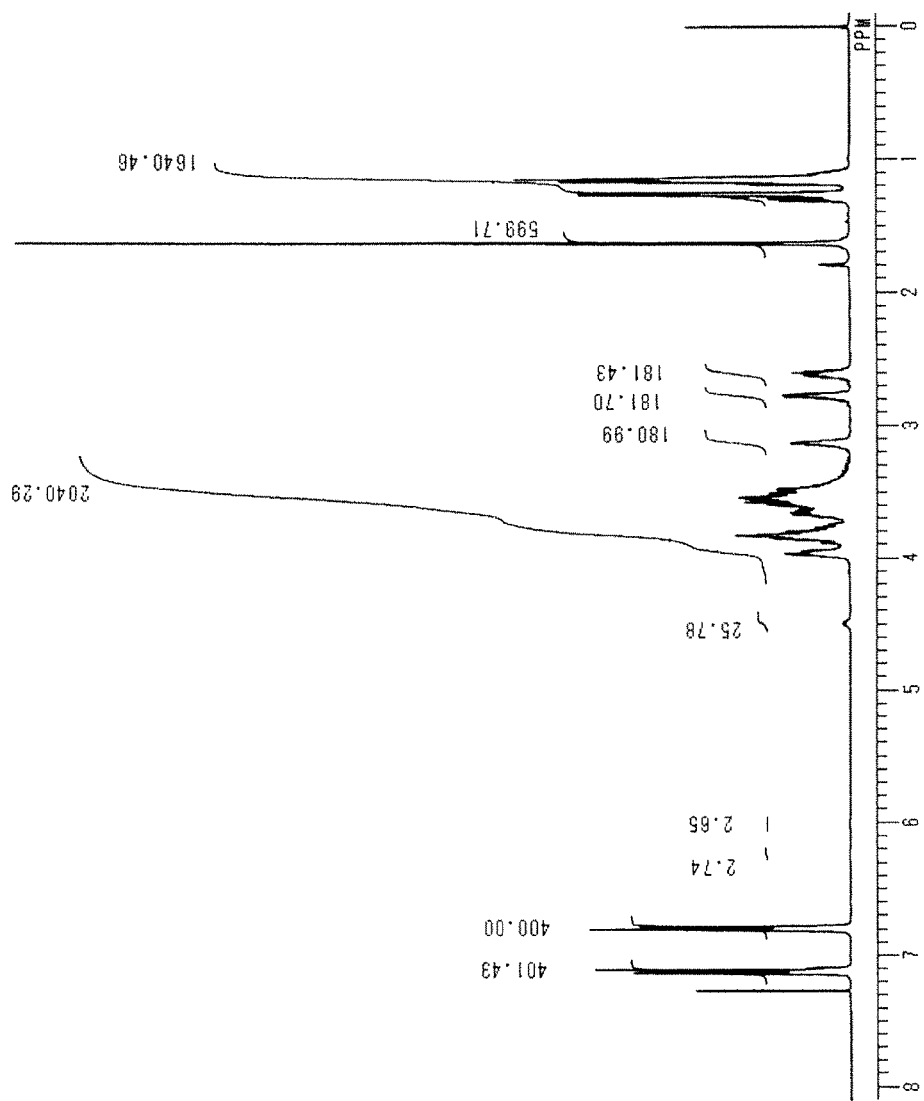
FIG. 1 shows an NMR chart of the epoxy resin composition A prepared in Example 1.

Hereinafter, the mode for carrying out the present invention (hereinafter, simply referred to as "the present embodiment") is described in detail. The following embodiment is an example for describing the present invention, and has no intention to limit the present invention to the following contents. The present invention can be implemented as appropriately modified within the scope of the gist thereof.

A first aspect of the present embodiment provides an epoxy resin composition comprising an epoxy resin represented by the following formula (1) and an epoxy resin represented by the following formula (2):

[Formula 10]

[Formula 11]

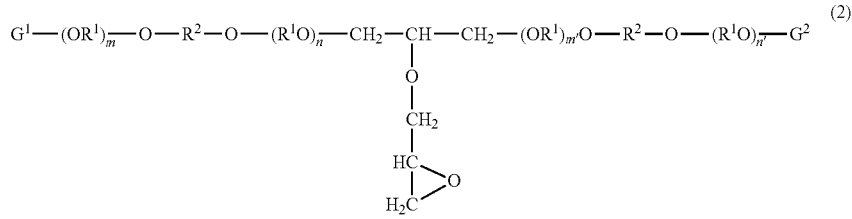

wherein m, n, m' and n' are each independently an integer of 1 to 30, $R^1$ and $R^2$ are each independently a divalent aliphatic group having 1 to 12 carbon atoms, or a divalent aromatic group having 6 to 40 carbon atoms, at least one of $R^1$ and $R^2$ represents a divalent aromatic group having 6 to 30 carbon atoms, $G^1$ represents a glycidyl group, and $G^2$ represents a hydrogen atom or a glycidyl group.

In formula (1), $R^1$ may be linear or branched. Additionally, $R^1$ may include an unsaturated bond group. The number of the carbon atoms of $R^1$ is preferably 1 to 6 from the viewpoint of the balance between the flexibility and the heat resistance, and is more preferably 1 to 3 from the viewpoint of the production easiness. Specific examples of $R^1$ include: an n-butylene group, a sec-butylene group, an isobutylene group, a tert-butylene group, an n-pentylene group, a 1-methylbutylene group, a 2-methylbutylene group, a 3-methylbutylene group, a 1-ethylpropylene group, a 1,1-dimethylpropylene group, a 1,2-dimethylpropylene group and 2,2-dimethylpropylene group. Among these, preferable specific examples thereof include a methylene group, an ethylene group, an n-propylene group and an isopropylene group. $R^1$s in formula (1) may be the same as each other or different from each other.

In formula (1), when $R^1$ is an aliphatic group, $R^2$ is preferably an aromatic group, and when $R^1$ is an aromatic group, $R^2$ is preferably an aliphatic group. $R^2$ is preferably a divalent aromatic group having 6 to 20 carbon atoms from the viewpoint of viscosity, and is more preferably a divalent aromatic group having 6 to 15 carbon atoms from the viewpoint of production easiness.

Specific examples of $R^2$ in formula (1) include: divalent aromatic groups each derived from any one selected from the group consisting of a phenylene group, a naphthylene group and a biphenylene; and bisphenol A, bisphenol F, bisphenol AD, tetrabromobisphenol A, biphenyl, tetramethylbiphenyl, tetrabromobiphenyl, diphenyl ether, benzophenone, phenyl benzoate, diphenyl sulfide, diphenyl sulfoxide, diphenyl sulfone, diphenyl disulfide, naphthalene, anthracene, hydroquinone, methylhydroquinone, dibutylhydroquinone, resorcinol, methylresorcinol and catechol.

$R^2$ in formula (1) is, from the viewpoint of heat resistance, preferably any one selected from the group consisting of a phenylene group, a naphthylene group and a divalent aromatic group having the structure represented by the following formula (3a):

[Formula 12]

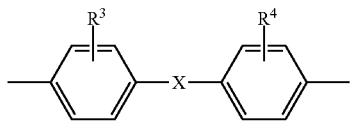

(3a)

wherein $R^3$ and $R^4$ each independently represent any one selected from the group consisting of a hydrogen atom, a halogen atom, a hydroxyl group, an alkoxy group having 1 to 12 carbon atoms, a carboxyl group and an alkyl group having 1 to 12 carbon atoms, and X represents any one selected from the group consisting of an alkylene group having 1 to 10 carbon atoms, —O—, —CO—, —COO—, —S—, —SO—, —SO$_2$— and —S—S—.

$R^3$ and $R^4$ are each independently, preferably a hydrogen atom, a chlorine atom, a hydroxyl group, a methyl group, an ethyl group, or a tert-butyl group, from the viewpoint of easy availability.

Specific examples of the divalent aromatic group having the structure represented by formula (3a) include: divalent aromatic groups each derived from any one selected from the group consisting of bisphenol A, bisphenol F, bisphenol AP, bisphenol AF, bisphenol B, bisphenol BP, bisphenol C, bisphenol E, bisphenol G, bisphenol M, bisphenol S, bisphenol P, bisphenol PH, bisphenol TMC, bisphenol Z, oxybiphenyl, dihydroxybenzophenone, 4-hydroxyphenyl 4-hydroxybenzoate, bis(4-hydroxyphenyl)sulfide, 4,4'-sulfinylbisphenol and bis(4-hydroxyphenyl)disulfide.

Examples of $R^1$ in formula (2) include the groups listed above as the specific examples of $R^1$ in formula (1). $R^1$ in formula (2) may be the same as or different from $R^1$ in formula (1).

Preferable specific examples of $R^1$ in formula (2) include an ethylene group, an n-propylene group and an isopropylene group. $R^1$s in formula (2) may be the same as each other or different from each other.

Examples of $R^2$ in formula (2) include the groups listed above as the specific examples of $R^2$ in formula (1). $R^2$ in formula (2) may be the same as or different from $R^2$ in formula (1). $R^2$s in formula (2) may be the same as each other or different from each other.

In formula (2), when $R^1$ is an aliphatic group, $R^2$ is preferably an aromatic group, and when $R^1$ is an aromatic group, $R^2$ is preferably an aliphatic group. $R^2$ in formula (2) is preferably a divalent aromatic group having 6 to 20 carbon atoms from the viewpoint of viscosity, and is more preferably a divalent aromatic group having 6 to 15 carbon atoms from the viewpoint of production easiness.

At least one of $R^2$ in formula (2) is, from the viewpoint of heat resistance, preferably any one selected from the group consisting of a phenylene group, a naphthylene group, a biphenylene group and a divalent aromatic group having the structure represented by the following formula (3b):

[Formula 13]

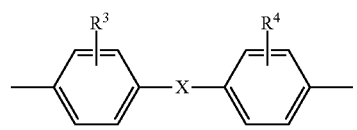

(3b)

wherein $R^3$ and $R^4$ each independently represent any one selected from the group consisting of a hydrogen atom, a halogen atom, a hydroxyl group, an alkoxy group having 1 to 12 carbon atoms, a carboxyl group and an alkyl group having 1 to 12 carbon atoms, and X represents any one selected from the group consisting of an alkylene group having 1 to 10 carbon atoms, —O—, —CO—, —COO—, —S—, —SO—, —SO$_2$— and —S—S—.

$R^3$ and $R^4$ are each independently, preferably a hydrogen atom, a chlorine atom, a hydroxyl group, a methyl group, an ethyl group, or a tert-butyl group, from the viewpoint of easy availability.

Formula (1) is preferably the following formula (4) from the viewpoint of impact resistance. Formula (2) is also preferably the following formula (5) from the viewpoint of impact resistance. More preferably, formula (1) is the following formula (4) and at the same time, formula (2) is the following formula (5). When formula (1) and formula (2) is a combination of such structures as described above, the heat resistance and the impact resistance are allowed to be compatible with each other at a still higher level, and for example, reflow resistance can also be more improved.

[Formula 14]

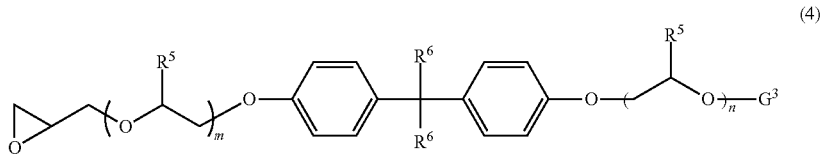

(4)

wherein $R^5$ and $R^6$ each independently represent a hydrogen atom or a methyl group, $G^3$ represents a hydrogen atom or a glycidyl group, and m and n are each independently an integer of 1 or more and satisfy the relation represented by $3 \leq (m+n) \leq 12$,

[Formula 15]

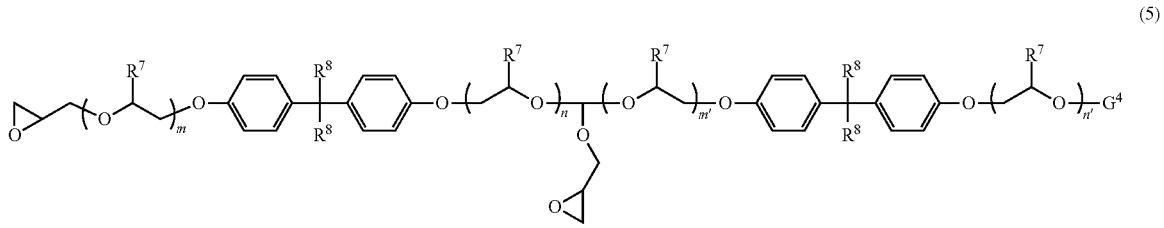

(5)

wherein $R^7$ and $R^8$ each independently represent a hydrogen, atom or a methyl group, $G^4$ represents a hydrogen atom or a glycidyl group, and m, n, m' and n' are each independently an integer of 1 or more and satisfy the relation represented by $6 \leq (m+n+m'+n') \leq 20$).

$G^4$ in formula (5) is more preferably a glycidyl group from the viewpoint of water absorbency and reaction rate.

The epoxy resin composition of the present embodiment preferably includes 100 parts by mass of the epoxy resin represented by formula (1) and 0.1 to 10 parts by mass of the epoxy resin represented by formula (2). When the content of the epoxy resin represented by formula (2) is 0.1 part by mass or more based on 100 parts by mass of the epoxy resin represented by formula (1), the cured product of the epoxy resin composition tends to sufficiently attain long-term adhesion reliability. When the content of the epoxy resin represented by formula (2) is 10 parts by mass or less based on 100 parts by mass of the epoxy resin represented by formula (1), the epoxy resin composition is allowed to be low in viscosity, and acquire when used as an adhesive, for example, a more improved handleability and at the same time, a more improved curability because of a large epoxy equivalent. The content of the epoxy resin represented by formula (2) is preferably 0.1 to 10 parts by mass and more preferably 0.5 to 9 parts by mass based on 100 parts by mass of the epoxy resin represented by formula (1).

As a second aspect of the present embodiment, here is quoted the epoxy resin represented by the following formula (1), wherein m and n in formula (1) are each independently an integer of 1 to 11 and satisfy the relation represented by $3 \leq (m+n) \leq 12$, and the proportion of the component having m and n satisfying the relation represented by $6 \leq (m+n) \leq 12$ in the epoxy resin is 30 mol % or more and 70 mol % or less:

[Formula 16]

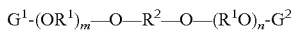

(1)

wherein m and n are each independently an integer of 1 to 30, $R^1$ and $R^2$ each independently represent an aliphatic group having 1 to 12 carbon atoms or a divalent aromatic group, at least one of $R^1$ and $R^2$ represents a divalent aromatic group having 6 to 30 carbon atoms, $G^1$ represents a glycidyl group, and $G^2$ represents a hydrogen atom or a glycidyl group.

By using such an epoxy resin, although the epoxy resin is low in viscosity, it is possible to obtain a cured product excellent in flexibility, adhesiveness and low water absorbency.

In formula (1), m and n are each independently an integer of 1 to 11, and preferably satisfy the relation represented by $3 \leq (m+n) \leq 12$. When (m+n) is 3 or more, the flexibility is more improved. When (m+n) is 12 or less, the viscosity can be made still lower, and hence the handleability is more improved.

In the epoxy resin of the present embodiment, the proportion of the component (hereinafter, sometimes referred to as the "component a") having m and n in formula (1) satisfying the relation of $6 \leq (m+n) \leq 12$ is 30 mol % or more and 70 mol % or less. When the proportion of the component a in the epoxy resin of the present embodiment is 30 mol % or more, a sufficient flexibility is obtained and the low water absorbency is achieved. When the proportion of the component a is 70 mol % or less, a low water absorbency and a low viscosity are achieved and excellent handleability is provided. The proportion of the component a is preferably 40 mol % or more and 60 mol % or less from the viewpoint of the balance between the flexibility and the viscosity. It is to be noted that m, n, (m+n) and the like described herein can be determined by the methods described in below-presented Examples.

In the epoxy resin of the present embodiment, the proportion of the component (hereinafter, sometimes referred to as the "component b") represented by formula (1) with $G^2$ being a glycidyl group is preferably 10 mol % or more and 100 mol % or less. When the proportion of the component b is 10 mol % or more, the curability is more improved.

$R^1$ in formula (1) may be linear or branched. Additionally, $R^1$ may include an unsaturated bond. The number of the carbon atoms of $R^1$ is preferably 1 to 6 from the viewpoint of the balance between the flexibility and the heat resistance, and is more preferably 1 to 4 from the viewpoint of the production easiness. Preferable specific examples of $R^1$ include an ethylene group, an n-propylene group and an isopropylene group. $R^1$s in formula (1) may be the same as each other or different from each other.

In formula (1), when $R^1$ is an aliphatic group, $R^2$ is preferably an aromatic group, and when $R^1$ is an aromatic group, $R^2$ is preferably an aliphatic group. $R^2$ is preferably a divalent aromatic group having 6 to 20 carbon atoms from the viewpoint of viscosity, and is more preferably a divalent aromatic group having 6 to 15 carbon atoms from the viewpoint of production easiness.

Specific examples of $R^2$ in formula (1) include: a phenylene group, a naphthylene group and a biphenylene group; and divalent aromatic groups each derived from any one selected from the group consisting of bisphenol A, bisphenol F, bisphenol AD, tetrabromobisphenol A, biphenyl, tetramethylbiphenyl, tetrabromobiphenyl, diphenyl ether, benzophenone, phenyl benzoate, diphenyl sulfide, diphenyl sulfoxide, diphenyl sulfone, diphenyl disulfide, naphthalene, anthracene, hydroquinone, methylhydroquinone, dibutylhydroquinone, resorcinol, methylresorcinol and catechol.

$R^2$ in formula (1) is, from the viewpoint of heat resistance, preferably any one selected from the group consisting of a phenylene group, a naphthylene group, a biphenylene group and a divalent aromatic group having the structure represented by the following formula (3a):

[Formula 17]

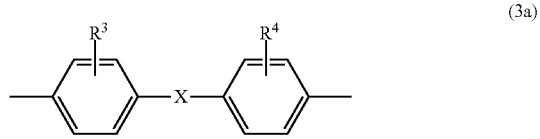

(3a)

($R^3$ and $R^4$ each independently represent a hydrogen atom, a halogen atom, a hydroxyl group, an alkoxy group having 1 to 12 carbon atoms, a carboxyl group or an alkyl group having 1 to 12 carbon atoms, and X represents any one selected from the group consisting of an alkylene group having 1 to 10 carbon atoms, —O—, —CO—, —COO—, —S—, —SO—, —SO$_2$— and —S—S—.)

$R^3$ and $R^4$ are each independently, preferably any one selected from the group consisting of a hydrogen atom, a chlorine atom, a bromine atom, a hydroxyl group, a methyl group, an ethyl group and a tert-butyl group, from the viewpoint of easy availability. $R^3$ and $R^4$ may be the same as each other or different from each other. Both of $R^3$ and $R^4$ are each preferably any one of a hydrogen atom, a chlorine atom, a bromine atom, a hydroxyl group, a methyl group, an ethyl group and a tert-butyl group.

Specific examples of the divalent aromatic group having the structure represented by formula (3a) include: divalent aromatic groups each derived from any one selected from the group consisting of bisphenol A, bisphenol F, bisphenol AD, tetrabromobisphenol A, diphenyl ether, benzophenone, phenyl benzoate, diphenyl sulfide, diphenyl sulfoxide, diphenyl sulfone and diphenyl disulfide.

Specific examples of $R^2$ in formula (2) include: a phenylene group, a naphthylene group and a biphenylene group; and divalent aromatic groups each derived from any one selected from the group consisting of bisphenol A, bisphenol F, bisphenol AD, tetrabromobisphenol A, biphenyl, tetramethylbiphenyl, tetrabromobiphenyl, diphenyl ether, benzophenone, phenyl benzoate, diphenyl sulfide, diphenyl sulfoxide, diphenyl sulfone, diphenyl disulfide, naphthalene, anthracene, hydroquinone, methylhydroquinone, dibutylhydroquinone, resorcinol, methylresorcinol and catechol.

The total chlorine content in the epoxy resin of the present embodiment is not particularly limited; however, the smaller the total chlorine content, for example, the more the reactivity, adhesiveness, mechanical strength, corrosion resistance and electric reliability tend to be improved. From such a viewpoint, the total chlorine content in the epoxy resin of the present embodiment is preferably 1000 ppm by mass or less, more preferably 500 ppm by mass or less and furthermore preferably 250 ppm by mass or less. In the present embodiment, the lower limit of the total chlorine content is not required to be particularly limited; however, for example, from the viewpoint of the balance between the obtained effect and the economic efficiency, the lower limit may be 1 ppm by mass or more. It is to be noted that the total chlorine content can be determined by the method described in below-presented Examples.

The epoxy resin of the present embodiment can be an epoxy resin composition further including the epoxy resin represented by the following formula (2):

[Formula 18]

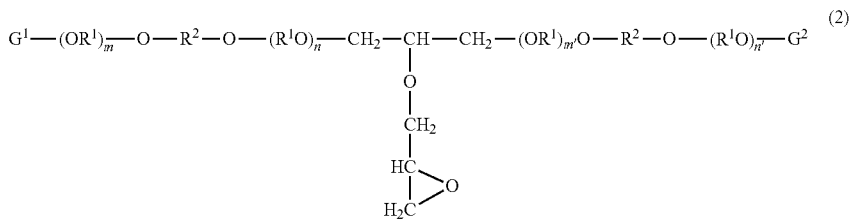

(2)

wherein m, n, m' and n' are each independently an integer of 1 to 30, $R^1$ and $R^2$ are each independently a divalent aliphatic group having 1 to 12 carbon atoms, or a divalent aromatic group, at least one of $R^1$ and $R^2$ represents a divalent aromatic group having 6 to 30 carbon atoms, $G^1$ represents a glycidyl group, and $G^2$ represents a hydrogen atom or a glycidyl group.

As the epoxy resin represented by formula (2), the same epoxy resin as described in the first embodiment can be used.

The mixing ratio between the epoxy resin of the present embodiment and the epoxy resin represented by formula (2) is not particularly limited; however, 100 parts by mass of the epoxy resin of the present embodiment and 0.1 to 10 parts by mass of the epoxy resin represented by formula (2) are preferably included. When the content of the epoxy resin represented by formula (2) is 0.1 part by mass or more based on 100 parts by mass of the epoxy resin of the present embodiment, the cured product of the epoxy resin composition tends to sufficiently provide a long-term adhesion reliability. When the content of the epoxy resin represented by formula (2) is 10 parts by mass or less based on 100 parts by mass of the epoxy resin of the present embodiment, the epoxy resin composition can be made low in viscosity, for example, the handleability is more improved when the epoxy resin composition is used as an adhesive, and at the same time, the curability is more improved because the epoxy equivalent becomes large. The content of the epoxy resin represented by formula (2) is preferably 0.1 to 10 parts by mass and more preferably 0.3 to 9 parts by mass based on 100 parts by mass of the epoxy resin represented by formula (1).

(Method for Producing Epoxy Resin and Others)

The epoxy resin composition(s) used in the epoxy resin composition of the above-described first embodiment and the epoxy resin of the second embodiment are the epoxy resins having at least the structure represented by formula (1). Hereinafter, an example of the method for producing the epoxy resin having the structure represented by formula (1) is described.

The epoxy resin can be obtained by the reaction yielding the epoxy resin represented by formula (1). Examples of the method for producing such an epoxy resin include a method in which a compound (hereinafter, also simply referred to as an "oxyalkylene adduct") prepared by adding an alkylene oxide to an aromatic compound having two phenolic hydroxyl groups in a ratio of 3 to 12 times the number of moles of the phenolic hydroxyl group to 2 moles of the phenolic hydroxyl group and epihalohydrin are allowed to react with each other in the presence of an alkaline compound.

Examples of the epihalohydrin include epichlorohydrin and epibromohydrin. The addition amount of the epihalohydrin is generally 1 to 10 equivalents and preferably 2 to 8 equivalents based on 1 equivalent of the alcoholic hydroxyl group of the oxyalkylene adduct.

Examples of the alkaline compound include sodium hydroxide, potassium hydroxide, barium hydroxide and potassium carbonate. These may be used each alone or in combinations of two or more thereof. The state of the alkaline compound is not particularly limited, and may be a solid state, a liquid state or an aqueous solution. The addition amount of the alkaline compound is generally 1 to 10 equivalents, preferably 1.5 to 7.5 equivalents and more preferably 2 to 5 equivalents based on 1 equivalent of the phenolic hydroxyl group or the alcoholic hydroxyl group.

In the present embodiment, from the viewpoint of promoting the reaction, it is preferable to use a phase transfer catalyst. In particular, the alkaline compound and the phase transfer catalyst are more preferably used in combination.

Examples of the phase transfer catalyst include: quaternary ammonium salts such as tetramethylammonium chloride, tetramethylammonium bromide, tetrapropylammonium chloride, tetrapropylammonium bromide, tetrabutylammonium chloride, tetrabutylammonium bromide, tetrabutylammonium iodide, benzyltrimethylammonium chloride, benzyltrimethylammonium bromide, benzyltriethylammonium chloride, benzyltriethylammonium bromide and phenyltrimethylammonium chloride; quaternary ammonium hydroxides such as tetramethylammonium hydroxide, tetrabutylammonium hydroxide and benzyltrimethylammonium hydroxide; crown ethers such as 15-crown-5, 18-crown-6, dibenzo-18-crown-6, dicyclohexyl-18-crown-6 and diaza-18-crown-6; and cryptands such as [2.1.1]-cryptand, [2.2.1]-cryptand, [2.2.2]-cryptand, [2.2.2]-decylcryptand and [2.2.2]-benzocryptand. These may be used each alone or in combinations of two or more thereof. The state of the phase transfer catalyst is not particularly limited, and may be a solid state, a liquid state, an aqueous solution or an alcohol solution.

The addition amount of the phase transfer catalyst is generally 0.25 to 10 moles and preferably 0.5 to 5 moles based on 1 mole of the phenolic hydroxyl group or the alcoholic hydroxyl group.

The reaction temperature is generally 20 to 100° C. and preferably 30 to 80° C. By setting the reaction temperature at 20° C. or higher, the reaction is made to proceed faster, and hence the glycidyl group of the epihalohydrin tends to be able to be efficiently introduced into the oxyalkylene adduct. By setting the reaction temperature at 100° C. or lower, the polymerization reaction of the epihalohydrin can be efficiently suppressed, and hence the glycidyl group of the epihalohydrin tends to be able to be efficiently introduced into the oxyalkylene adduct.

The reaction time is generally 1 to 12 hours, preferably 1.5 to 8 hours and more preferably 2 to 6 hours.

After the completion of the reaction, the produced salt, the residual alkaline compound, the residual phase transfer catalyst and the like are removed from the reaction solution by, for example, washing with water. Subsequently, the reaction solution is heated at normal pressure or under reduced pressure to remove the residual epihalohydrin and the epoxy resin is collected.

When the total chlorine content of the epoxy resin is intended to be more removed, for example, the collected epoxy resin as described above is dissolved in a solvent such as toluene or methyl isobutyl ketone, and then the alkaline compound (the compound can be in a state such as a solid state, a liquid state or a solution state) is newly added. Thus, the ring closure reaction of the epihalohydrin is allowed to proceed and the hydrolytic chlorine amount can be more reduced. In this case, the addition amount of the alkaline compound is generally 0.5 to 5 equivalents and preferably 1 to 3 equivalents based on 1 equivalent of hydrolytic chlorine. Generally, the reaction temperature of the ring closure reaction is preferably 60 to 120° C., and the reaction time is preferably 0.5 to 3 hours.

The epoxy resin is excellent in compatibility, and hence can be suitably used as epoxy resin compositions including other added components.

Next, an example of the method for producing the epoxy resin having at least the structure represented by formula (2) is described. The epoxy resin having the structure represented by formula (2) can also be obtained by appropriately controlling the production conditions in the method shown as an example of the method for producing the epoxy resin represented by formula (1). Additionally, by making larger the amount of epihalohydrin based on the alcoholic hydroxyl group at the time of production, the yield of the epoxy resin having the structure represented by formula (2) can also be improved. In particular, by further adding the epihalohydrin during the reaction, the yield of the epoxy resin represented by formula (2) tends to be able to be more improved.

It is possible to realize an epoxy resin composition including the epoxy resin composition of the first embodiment and/or the epoxy resin of the second embodiment and a curing agent. The resulting epoxy resin composition may further include, if necessary, another epoxy resin, a curing promoting agent and the like.

Examples of the curing agent include, without being limited to: an amine curing agent, an amide curing agent, an acid anhydride curing agent, a phenolic curing agent, a latent curing agent and a catalyst-based curing agent.

Examples of the amine curing agent include an aliphatic amine and an aromatic amine. Examples of the aliphatic amine include: diethylenetriamine, triethylenetetramine, tetraethylenepentamine, m-xylene diamine, trimethylhexamethylenediamine, 2-methylpentamethylenediamine, isophoronediamine, 1,3-bisaminomethylcyclohexane, bis(4-aminocyclohexyl)methane, norbornenediamine and 1,2-diaminocyclohexane. Examples of the aromatic amine include: diaminodiphenylmethane, m-phenylenediamine, diaminodiphenylsulfone, diethyltoluenediamine, trimethylene bis(4-amino benzoate) and polytetramethylene oxide-di-p-amino benzoate.

Examples of the amide curing agent include: dicyandiamide and the guanidine compounds as the derivatives thereof, or the curing agents prepared by adding acid anhydrides to amine curing agents.

Examples of the acid anhydride curing agent include: phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride and methylhexahydrophthalic anhydride.

Examples of the phenolic curing agent include: phenol novolac resin, cresol novolac resin, phenol aralkyl resin, cresol aralkyl resin, naphthol aralkyl resin, biphenyl-modified phenol resin, biphenyl-modified phenol aralkyl resin, dicyclopentadiene-modified phenol resin, aminotriazine-modified phenol resin, naphthol novolac resin, naphthol-phenol co-condensed novolac resin, naphthol-cresol co-condensed novolac resin and allyl acrylate phenolic resin.

Examples of the latent curing agent include: imidazoles, dicyandiamides and derivatives thereof, imidazole latent curing agents and capsulated amine adducts. For these, commercial products can also be used; examples of the commercial products include: Amicure Series (manufactured by Ajimomoto Fine-Techno Co., Ltd.) such as "PN23," "PN-40," and "PN-H"; and Nova Cure Series (manufactured by Asahi Kasei E-Materials Corp.) such as "HX-3088," "HX-3941," and "HX-3742."

Examples of the catalyst-based curing agent include cationic thermosetting catalysts and $BF_3$-amine complexes. These curing agents may be used each alone or in combinations of two or more thereof.

Among the above-described curing agents, amine curing agents are preferable when the flexibility and the adhesiveness are regarded as important. On the other hand, phenolic curing agents are preferable when the heat resistance and the low water absorbency are regard as important.

The content of the curing agent in the epoxy resin composition is preferably 1 to 100 parts by mass and more preferably 2 to 90 parts by mass based on 100 parts by mass of the total amount of the epoxy resin. In particular, for the amine curing agents, amide curing agents, acid anhydride curing agents and phenolic curing agents, the content of the curing agent in the epoxy resin composition is preferably 0.7 to 1.5 equivalents based on 1 equivalent of the glycidyl group of the epoxy resin. In the case of a latent curing agent, the amount of the curing agent is preferably 5 to 50 parts by mass based on 100 parts by mass of the epoxy resin. In the case of a catalyst-based curing agent, the amount of the curing agent is preferably 0.5 to 6.0 parts by mass based on 100 parts by mass of the epoxy resin. Within the above-described ranges, the curing reaction is allowed to proceed efficiently, and more satisfactory curing physical properties tend to be developed.

In the resin composition of the present embodiment, epoxy resins other than the above-described epoxy resins may be used in combination, as the components other than the curing agent. Examples of the structures of the resins usable in combination as the other resins include: bifunctional epoxy resins such as bisphenol A epoxy resin, bisphenol F-based epoxy resin, bisphenol AD-based epoxy resin, tetrabromobisphenol A-based epoxy resin, biphenyl-based epoxy resin, tetramethylbiphenyl-based epoxy resin, tetrabromobiphenyl-based epoxy resin, diphenylether-based epoxy resin, benzophenone-based epoxy resin, phenyl benzoate-based epoxy resin, diphenyl sulfide-based epoxy resin, diphenyl sulfoxide-based epoxy resin, diphenyl sulfone-based epoxy resin, diphenyl disulfide-based epoxy resin, naphthalene-based epoxy resin, anthracene-based epoxy resin, hydroquinone-based epoxy resin, methylhydroquinone-based epoxy resin, dibutylhydroquinone-based epoxy resin, resorcin-based epoxy resin, methylresorcin-based epoxy resin, catechol-based epoxy resin, and N,N-diglycidylaniline-based epoxy resin; trifunctional epoxy resins such as N,N-diglycidylaminobenzene-based epoxy resin, o-(N,N-diglycidylamino)toluene-based epoxy resin and triazine-based epoxy resin; quadrafunctional epoxy resins such as tetraglycidylaminodiphenyl methane-based epoxy resin and diaminobenzene-based epoxy resin; multifunctional epoxy resins such as phenol novolac-based epoxy resin, cresol novolac-based epoxy resin, triphenylmethane-based epoxy resin, tetraphenylethane-based epoxy resin, dicyclopentadiene-based epoxy resin, naphtholaralkyl-based epoxy resin and brominated phenol novolac-based epoxy resin; and alicyclic epoxy resins. Additionally, the epoxy resins obtained by modifying these resins with isocyanate or the like can also be used in combination.

The content of the other resin(s) is preferably 95% by mass or less and more preferably 80% by mass or less of the whole epoxy resin components in the epoxy resin composition of the present embodiment.

The epoxy resin composition of the present embodiment may further include a curing promoting agent. Specific examples of the curing promoting agent include: imidazole curing promoting agents such as 2-methylimidazole, 2-ethylimidazole and 2-ethyl-4-methylimidazole; tertiary amine curing promoting agents such as 2-(dimethylaminomethyl) phenol, 1,5-diazabicyclo[4.3.0]non-5-ene and 1,8-diazabicyclo[5.4.0]undec-7-ene; phosphorus-based curing promoting agents such as triphenylphosphine; organic acid metal salts; Lewis acids; and amine complex salts. The combinational use of these with the above-described curing agents enables further promotion of the curing reaction. According to the types of the above described curing agents, appropriate types of the curing promoting agents can be selected.

The content of the curing promoting agent in the epoxy resin composition of the present embodiment is not particularly limited as long as the content falls within a range allowing the advantageous effects of the present embodiment to be achieved. Usually, the content of the curing promoting agent is preferably 0.1 to 5.0 parts by mass based on 100 parts by mass of the total amount of the epoxy resin. By setting the content of the curing promoting agent so as to fall within the above-described range, the curing reaction can be sufficiently promoted, and at the same time, more satisfactory curing physical properties tend to be obtained.

The epoxy resin composition of the present embodiment may further include, if necessary, an inorganic filler. Specific examples of the inorganic filler include fused silica, crystalline silica, alumina, talc, silicon nitride and aluminum nitride.

The content of the inorganic filler in the epoxy resin composition of the present embodiment is not particularly limited as long as the content falls within a range allowing the advantageous effects of the present embodiment to be achieved. Usually, the content of the inorganic filler is preferably 90% by mass or less of the epoxy resin composition of the present embodiment. By setting the content of the inorganic filler so as to fall within the above-described range, the epoxy resin composition tends to be sufficiently low in viscosity and excellent in handleability.

The epoxy resin composition of the present embodiment may further include, if necessary, other additives such as a flame retardant, a liquid stress agent, a silane coupling agent, a diluent, a leveling agent, a release agent and a pigment. These additives can be appropriately selected so as to be suitable within the ranges allowing the advantageous effects of the present embodiment to be achieved.

Examples of the flame retardant include a bromine-based flame retardant, a phosphorus-based flame retardant, a nitrogen-based flame retardant and an inorganic flame retardant. Examples of the bromine-based flame retardant include tetrabromophenol. Examples of the phosphorus-based flame retardant include 9,10-dihydro-9-oxa-10-phosphaphenanthrene-10-oxide and the epoxy derivatives thereof, triphenylphosphine and the derivatives thereof, phosphoric acid esters, condensed phosphoric acid esters and phosphazene compounds. Examples of the nitrogen-based flame retardant include a guanidine flame retardant, a triazine structure-containing phenol, polyphosphoric acid melamine and isocyanuric acid. Examples of the inorganic flame retardant include magnesium hydroxide and aluminum hydroxide; from the viewpoint of heat resistance, magnesium hydroxide is preferable.

The content of the flame retardant is not particularly limited, but is preferably 5 to 200% by mass and more preferably 10 to 100% by mass.

Examples of the liquid low stress agent include: polyalkylene glycols and the amine-modified products thereof; organic rubbers such as polybutadiene and acrylonitrile; silicone rubbers such as dimethylsiloxane; and silicone oils. These may be used each alone or in combinations of two or more thereof. The content of the liquid state low stress agent is not particularly limited, but is preferably 5 to 40% by mass and more preferably 10 to 20% by mass based on the epoxy resin.

Examples of the silane coupling agent include: silane coupling agents such as 3-glycydoxypropyltrimethoxysilane, 3-glycydoxypropylmethyldimethoxysilane, 2-(3,4-epoxycyclohexyl)ethyltrimethoxysilane, N-phenyl-γ-aminopropyltrimethoxysilane, N-(2-aminoethyl)3-aminopropylmethyldimethoxysilane, N-(2-aminoethyl)-3-aminopropylmethyltrimethoxysilane, 3-aminopropyltriethoxysilane, 3-mercaptopropyltrimethoxysilane, vinyltrimethoxysilane, N-(2-(vinylbenzylamino)ethyl)-3-aminopropyl-trimethoxysilane hydrochloride, 3-methacryloyloxypropyltrimethoxysilane, 3-chloropropylmethyldimethoxysilane and 3-chloropropyl trimethoxysilane. Among these, from the viewpoint of adhesion strength, polymerizable functional group-containing silane coupling agents are preferable.

Examples of the diluent include: acryl group-containing multifunctional acrylate compounds; and monofunctional glycidyl group-containing glycidyl-based reactive diluents. These may be used each alone or in combinations of two or more thereof. The content of the diluent is not particularly limited, but is preferably 1 to 40% by mass and more preferably 5 to 30% by mass based on the epoxy resin.

Examples of the leveling agent include a silicone leveling agent and an acrylic leveling agent.

The cured product of the present embodiment is obtained by thermally curing the epoxy resin composition. In other words, examples of the cured product of the present embodiment include the cured product obtained by curing the above-described epoxy resin composition. For example, it is also possible to obtain an epoxy resin composition by mixing a curing agent, and if necessary, a curing promoting agent, an inorganic filler, an additive and the like with the epoxy resin or the epoxy resin composition or the present embodiment, to such an extent that the resulting mixture is uniform, by using an extruder, a kneader, a toll or the like. Subsequently, a cured product can be obtained by molding the epoxy resin composition by using a cast molding machine, a transfer molding machine, an injection molding machine or the like, and by further heating the resulting molded product under the conditions of about 80 to 200° C. and about 2 to 10 hours.

Alternatively, the epoxy resin composition of the present embodiment is dissolved in a solvent such as toluene, xylene, acetone, methyl ethyl ketone or methyl isobutyl ketone, a substrate such as glass fiber, carbon fibe r, polyester fiber, polyamide fiber, alumina fiber or paper is impregnated with the resulting solution, and the impregnated substrate is dried by heating to yield a prepreg. A cured product can also be obtained by hot press molding the obtained prepreg.

A cured product obtained from the epoxy resin represented by the following formula (1):

[Formula 19]

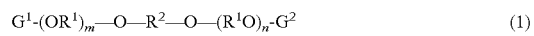

$$G^1\text{-}(OR^1)_m\text{—}O\text{—}R^2\text{—}O\text{—}(R^1O)_n\text{-}G^2 \quad (1)$$

wherein, in formula (1), m and n are each independently an integer of 1 to 30, $R^1$ and $R^2$ each independently represent an aliphatic group having 1 to 12 carbon atoms or a divalent aromatic group, at least one of $R^1$ and $R^2$ represents a divalent aromatic group having 6 to 30 carbon atoms, $G^1$ represents a glycidyl group, and $G^2$ represents a hydrogen atom or a glycidyl group, $$E'/(273+T^1/3)<8.5 \quad (a)$$

wherein, in mathematical expression (a), $T^1$ is the obtained peak top temperature of the loss tangent, and E' (MPa) is the storage modulus measured at 30° C., $$E'(T^1-20)>10\times E'(T^1+20) \quad (b)$$

wherein, in mathematical expression (b), $E'(T^1-20)$ is the storage modulus measured at $(T^1-20)°$ C., and $E'(T^1+20)$ is the storage modulus measured at $(T^1+20)°$ C.

Such a cured product as described above is excellent in the physical properties such as drop impact resistance, small in the degradation of the adhesion strength due to temperature variation, and thus significantly contribute to the reliability after mounting. Such a cured product can also be obtained by using, for example, the above-described epoxy resin composition of the first embodiment or the epoxy resin of the second embodiment.

The cured product preferably further satisfies the relation represented by mathematical expression (c) or the relation represented by mathematical expression (d). The cured product preferably further satisfies both of the relation represented by mathematical expression (c) and the relation represented by mathematical expression (d). The cured product satisfying these relations can more suppress the degradation of the adhesive force due to temperature variation.

The epoxy resin composition and the epoxy resin of the present embodiment, and the cured products obtained from these can be used in various applications in which epoxy resins have hitherto been used as materials. For example, these epoxy resin composition, epoxy resin and cured products are particularly useful in the applications to electronic parts (for example, sealants, adhesives, printed substrate materials, coating materials and composite materials). Among these, these epoxy resin composition, epoxy resin and cured products are suitably used for semiconductor sealants such as underfill and molding, adhesives, bonding pastes and bonding films (for example, inter-layer insulating materials); electrically conductive materials; electrically conductive adhesives such as anisotropic electrically conductive films (ACFs) and the like; insulating materials; photosensitive materials such as solder resist and cover lay film; and printed wiring boards. In addition, these epoxy resin composition, epoxy resin and cured products are suitably used as coating materials, prepregs, thermally conductive materials, fuel cell sealing materials and the like.

Adhesives, bonding pastes and bonding films obtained from the epoxy resin composition, the epoxy resin and the like of the present embodiment are useful for liquid adhesives, film-type adhesives, die bonding materials and the like. Examples of the method for producing a film-type adhesive include the methods described in Japanese Patent Laid-Open Nos. 62-141083 and 05-295329.

For example, a solution is prepared by dissolving a solid epoxy resin, a liquid epoxy resin or the like in a solvent such as toluene. In this case, the content of the solid epoxy resin or the liquid epoxy resin is preferably controlled so as to be about 50% by mass. In addition to these epoxy resins, a solid urethane resin or the like may also be mixed. Also in the case where a urethane resin or the like is mixed, the total resin content is preferably controlled so as to be about 50% by mass.

Then, to this solution, a curing agent for epoxy resin is further added to yield a varnish. As the curing agent for epoxy resin, a single curing agent may be used alone or two or more curing agents may be used in combination. In this case, the total content of the curing agent(s) for the epoxy resin in the varnish is preferably about 30% by mass. The varnish is applied to, for example, a 50-μm thick ethylene terephthalate substrate for release, then the solvent (such as toluene) is dried to form a coating film. In this case, the thickness of the coating film is preferably controlled so as to be about 30 μm. By drying the solvent (such as toluene) in the varnish, it is possible to obtain a bonding film which is inactive at normal temperature and exhibits adhesiveness by heating.

Examples of the electrically conductive material include electrically conductive films and electrically conductive pastes. Examples of the anisotropic electrically conductive materials include anisotropic electrically conductive films and anisotropic electrically conductive pastes. As the method for producing these, for example, the method described in Japanese Patent Laid-Open No. 01-113480 can be adopted. For example, at the time of the preparation of the varnish described in the production of the foregoing bonding film, an electrically conductive material and an anisotropic electrically conductive material are also mixed to prepare a coating liquid. The coating liquid is applied to the substrate and then dried, an electrically conductive film or an anisotropic electrically conductive film can be produced. Examples of the electrically conductive particles include: a solder particle; a nickel particle; a nano-size metal crystal; a composite particle in which the surface of a metal is coated with another metal; an inclined particle of copper and silver; and a particle in which the surface of a resin particle (such as a resin particle of styrene resin, urethane resin, melamine resin, epoxy resin, acrylic resin, phenolic resin, or styrene-butadiene resin) is coated with an electrically conductive thin film (such as, a film of gold, nickel, silver, copper or a solder). Usually, an electrically conductive particle is a nearly spherical microparticle having an average particle size of 1 to 20 μm. Examples of the substrate in forming a film include: substrates each made of polyester, polyethylene, polyimide or polytetrafluoroethylene.

Examples of the insulating material include insulating adhesive films and insulating adhesive pastes. By using the above-described bonding film, an insulating adhesive film, which is an insulating material, can be obtained. An insulating adhesive paste can be obtained by mixing an insulating filler of the above-described fillers with a one-component epoxy resin composition, in addition to the use of a sealing material.

Examples of the sealant include a solid sealant, a liquid sealant and a film-type sealant. The liquid sealant is useful as an underfill material, a potting material, a dam material and the like. As the method for producing a sealant, for example, the methods described in Japanese Patent Laid-Open Nos. 05-043661 and 2002-226675 can be adopted. More specifically, a sealant can be obtained by adding a curing agent such as methylhexahydrophthalic anhydride to the epoxy resin composition or the epoxy resin of the present embodiment and by uniformly mixing the resulting mixture. In addition to the curing agent, for example, a spherical fused silica powder can also be added.

As the method for producing the photosensitive material, for example, the method described in Japanese Patent Laid-Open No. 2008-250305 can also be adopted. For example, a photosensitive material can be obtained by uniformly mixing a carboxyl group-containing alkali-soluble polymer, an ethylenically unsaturated addition polymerizable monomer, a photopolymerization initiator or the like with the epoxy resin composition or the epoxy resin of the present embodiment.

Examples of the material for coating include: coating materials for electronic materials, overcoating materials for covering printed wiring boards, and inter-layer insulating resin compositions for printed boards. As the method for producing the coating material, for example, the methods described in National Publication of International Patent Application No. 1992-006116, and Japanese Patent Laid-Open Nos. 07-304931, 08-064960 and 2003-246838. More specifically, by dissolving the epoxy resin composition or the epoxy resin of the present embodiment, a filler such as silica and a curing agent for epoxy resin in a solvent (such as methyl ethyl ketone (MEK)), a solution having a concentration of 50% of the solid content inclusive of the resin and the filler is prepared. With the solution, resins (such as other epoxy resins, a phenoxy resin or a rubber-modified epoxy resin) other than the above-described epoxy resin may also be mixed. The solution is applied to a polyimide film in a thickness of 50 μm, a copper foil is superposed and laminated on the applied solution layer at 60 to 150° C. The resulting laminated product is heated and cured at 180 to 200° C., and thus a laminated plate subjected to inter-layer coating with the epoxy resin composition can be obtained.

As the method for producing the coating material composition, for example, the methods described in Japanese Patent Laid-Open Nos. 11-323247 and 2005-113103. More specifically, for example, the epoxy resin of the present embodiment and titanium dioxide or talc are dissolved in a mixed solvent (such as, methyl isobutyl ketone (MIBK)/xylene=1/1, volume ratio) to prepare a base component. By adding a curing agent for epoxy resin to the base component, and by uniformly dispersing the curing agent in the base component, a coating material composition can be obtained.

As the method for producing the prepreg, for example, the methods described in Japanese Patent Laid-Open No. 09-071633 and International Publication No. WO98/44017 can be adopted. Examples of such a method include a method in which a reinforced substrate is impregnated with an epoxy resin composition and the substrate is heated to yield a prepreg. Examples of the solvent in the varnish to be impregnated include methyl ethyl ketone, acetone, ethyl cellosolve, methanol, ethanol and isopropyl alcohol. These solvents are preferably made not to remain in the prepreg. The type of the reinforced substrate is not particularly limited; however, examples of the reinforced substrate include paper, glass fabric, glass non-woven fabric, aramid fabric and liquid crystal polymer. The proportions of the resin composition and the reinforced substrate are not particularly limited; however, usually, the content of the resin in the prepreg is preferably 20 to 80% by mass. A composite material can be obtained by superposing several sheets of the prepreg and by heat molding the resulting laminate.

As the method for producing the thermally conductive material, for example, the methods described in Japanese Patent Laid-Open Nos. 06-136244, 10-237410 and 2000-003987 can be adopted. More specifically, a thermally conductive resin paste can be obtained by uniformly kneading the epoxy resin composition or the epoxy resin of the present embodiment, a curing agent (such as a phenol novolac curing agent) and a thermally conductive filler (such as a graphite powder).

As the method for producing the fuel cell sealing material, the methods described in Japanese Patent Laid-Open Nos. 2002-332328 and 2004-075954 can be adopted. More specifically, a mixture is obtained by mixing the epoxy resin composition or the epoxy resin of the present embodiment and an electrically conductive material (such as an artificial graphite material) with a mixer or the like. A composition is obtained by uniformly mixing a curing agent for epoxy resin with the obtained mixture. A fuel cell sealing material can be obtained by compression molding the composition under the conditions of a mold temperature of 170 to 190° C. and a molding pressure of 150 to 300 kg/cm$^2$. The fuel cell sealing material has a practically sufficient electrical conductivity and is excellent in gas barrier property and molding processability.

As the method for producing the overcoating material for flexible wiring board, for example, the methods described in International Publication No. WO 00/64960 and Japanese Patent Laid-Open No. 2006-137838 can be adopted. More specifically, first, a composition is obtained by uniformly dispersing the epoxy resin composition or the epoxy resin of the present embodiment, a carboxyl-modified polybutadiene to react with these, rubber particles, a curing agent for epoxy resin and a curing promoting agent. A solution of an overcoating material for flexible wiring board is prepared by dissolving the composition in methyl ethyl ketone (MEK). Further, an aqueous solution of a dicarboxylic acid (such as succinic acid) is added to the solution of an overcoating material for flexible wiring board. An overcoating material for flexible wiring board can be obtained by applying the solution of the overcoating material to a polyimide film, followed by drying the applied solution. In this case, the film thickness after drying is preferably controlled so as to be about 25 μm.

EXAMPLES

Hereinafter, the present invention is described more specifically by way of Examples and Comparative Examples; however, the present invention is not limited at all by Examples and Comparative Examples. It is to be noted that "parts," "%," and "ppm" are based on mass unless otherwise specified. Hereinafter, commercially available reagents were used without purification unless otherwise specified.

The components and the like used in present Examples were as follows.

"Epolite 40E": Ethylene glycol diglycidyl ether (epoxy equivalent: 135 g/eq., viscosity: 40 mPa·s, glycidylation ratio: 96 mol %, total chlorine content: 18220 ppm by mass, manufactured by Kyoeisha Chemical Co., Ltd.)

"YED216D": 1,6-Hexamethylene diglycidyl ether (epoxy equivalent: 120 g/eq., manufactured by Mitsubishi Chemical Corp.)

"AER260": Bisphenol A-based epoxy resin (manufactured by Asahi Kasei E-Materials Corp., epoxy equivalent 188 g/eq.)

"AER6011": Sold bisphenol A-based epoxy resin (epoxy equivalent: 425 g/eq., manufactured by Asahi Kasei E-Materials Corp.)

"YL983U": Bisphenol F-based epoxy resin (epoxy equivalent: 170 g/eq., manufactured by Mitsubishi Chemical Corp.)

"Diaminodiphenylmethane" (amine equivalent: 49.6 g/eq., manufactured by Wako Pure Chemical Industries, Ltd.)

"Ethacure 100": Aromatic amine (amine equivalent: 44.5 g/eq., manufactured by Mitsui Fine Chemicals, Inc.)

"MEH8000H": Liquid phenol resin (phenol equivalent: 142 g/eq., manufactured by Meiwa Plastic Industries, Ltd.)

"Rikacid MHT": 4-Methylhexahydrophthalic anhydride (acid anhydride equivalent: 168 g/eq., manufactured by New Japan Chemical Co., Ltd.)

"HX3941": Microcapsule-type curing agent (amine adduct-based microcapsule-type curing agent, manufactured by Asahi Kasei E-Materials Corp.)

"AC-5V": Silica (average particle size: 5 μm, manufactured by Tatsumori Ltd.)

"KBM-403": Silica surface treatment agent (epoxy-based silane coupling agent, manufactured by Shin-Etsu Chemical Co., Ltd.)

The measurement methods of the respective physical properties were as follows.

(Epoxy Equivalent)

The epoxy equivalent was measured according to JIS K7236.

(Total Chlorine Content)

The total chlorine content was measured according to JIS K7243-3.

(Hydrolytic Chlorine Content)

The hydrolytic chlorine content was measured according to JIS K7243-2.

(Verification of Structures of Epoxy Resin Composition and Epoxy Resin, and Others)

The verification of the structures of the epoxy resin composition and the epoxy resin, and relevant matters was performed by using a high performance liquid chromatograph (HPLC) and a mass spectroscope (MS). For example, the proportion related to m and n in formula (1), namely, (m+n) in formula (1), and the structure represented by formula (1) were verified. The proportion related to m, n, m and n' in formula (2) and the structure represented by formula (2) were also verified similarly.

The HPLC measurement conditions were as follows.
"LC8020 model II" system manufactured by Tohso Corp.
Column: "OVA PACK C18" manufactured by Waters Corp.
Mobile phase; Distilled water/acetonitrile (the mixing proportion was changed at a constant rate between 0 minute and 20 minutes, so as the ratio distilled water/acetonitrile=50/50 to 0/100 (volume ratio).)
Flow rate: 1.5 mL/min
Detector: 280 nm
The measurement conditions of MS were as follows.
"LCQ" apparatus manufactured by Thermo Electron Corp.
Ionization method: Atmospheric pressure photochemical ionization method (APCI)
Scan range: m/z=150 to 2000

It is to be noted that, for example, the values of m, n and (m+n) were determined from the respective peak areas in the obtained HPLC and GC charts.

(Viscosity)

The viscosity was measured according to JIS K7117-2 (E-type viscometer).

(Identification and Calculation of Contents of Component Represented by Formula (1) and Component Represented by Formula (2) and Others)

By using a high performance liquid chromatograph (HPLC) and a mass spectroscope (MS), the numerical value of (m+n) in formula (1), the numerical value of (m+n+m'+n') in formula (2) and the like were determined.

The measurement conditions of HPLC were as follows.
Measurement apparatus: "LC8020 model II" system manufactured by Tosoh Corp.
Column: "NOVA PACK C18" manufactured by Waters Corp.
Mobile phase; Distilled water/methanol/acetonitrile (the mixing proportion was changed at a constant rate between 0 minute and 20 minutes, so as the ratio distilled water/acetonitrile=50/50 to 0/100 (volume ratio).),
Flow rate: 1.5 mL/min
Detector: 280 nm
The measurement conditions of MS were as follows.
Measurement apparatus: "LCQ" apparatus manufactured by Thermo Electron Corp.
Ionization: APCI+
Scan range: m/z=150 to 2000

The above-described respective numerical values and contents were determined from the respective peak areas in the obtained HPLC and MS charts.

(Evaluation of Compatibility)

The epoxy resin "AER4152" (oxazolidone ring-containing isocyanate-modified epoxy resin, epoxy equivalent: 340 g/eq., manufactured by Asahi Kasei Epoxy Co., Ltd.) and a below-described synthetic resin were mixed with each other in a mass ratio of 50/50, and heated at 140° C. The compatibility was evaluated when the mixture was cooled to room temperature. The compatibility was evaluated on the basis of the following standards.

◯: The whole mixture was transparent and exhibited a uniform phase.

Δ: The mixture was partially of a marble pattern, but was transparent as a whole and the whole mixture was at a level practically free from problems.

X: The whole mixture became clouded, and exhibited a non-uniform phase.

(Viscoelasticity)

Each of the epoxy resin compositions prepared according to Table 2 was cured at 180° C. for 2 hours to yield a cured product. Each of the obtained cured products was cut with a diamond cutter and a 10 mm×40 mm×0.5 mm specimen was obtained. Each of these specimen was set in a solid viscoelasticity measurement apparatus (DMA, "RSA-G2" manufactured by TA Instruments, Inc.), and the measurement was performed under the measurement condition of the temperature range from −50 to 300° C. (temperature increase rate: 2° C./rain). The temperature at which tan δ became the maximum value was taken as the glass transition point (Tg)=$T_1$. From the obtained measurement results, the storage modulus E' at 30° C., the storage modulus E'(Tg−20) at (Tg−20)° C. and the storage modulus E'(Tg+20) at (Tg+20)° C. were respectively determined.

(Bending Strength)

The bending strength of each of the cured products was measured according to JIS K7116.

(Fracture Toughness (KIc) Test)

The fracture toughness of each of the cured products was measured according to JIS K6911.

(Copper Plate Shear Adhesion Strength)

The copper plate shear adhesion strength of each of the cured products was measured according to JIS K6850. A 100-μm thick fluororesin heat resistant tape was bonded to the surface of the standard specimen C1100P (manufactured by Nippon Testpanel Co., Ltd.) so as to form a 25 mm×5 mm gap on the surface of the standard specimen. In the gap (25 mm×5 mm), the epoxy resin composition was applied, and the applied epoxy resin composition was sandwiched between the masked specimen and another piece of the standard specimen C1100P. The sandwiched epoxy resin composition was heated under the conditions of 180° C. and 2 hours, to thermally cure the epoxy resin composition, and thus a sample was obtained.

For the obtained sample, the copper plate shear adhesion strength (a) before the heat cycle test was measured in a constant-temperature and constant-humidity chamber set at 23° C. and 50% RH, by using the tensile tester AGS-H 5 kN.

The obtained sample was subjected to 1000 cycles of a heat cycle test between −40° C. (maintained for 15 minutes) and +125° C. (maintained for 15 minutes). Then, the copper plate shear adhesion strength (b) after the heat cycle test was measured.

The adhesion strength retention rate (b/a) was obtained by calculating the ratio of the copper plate shear adhesion strength (b) after the heat cycle test to the copper plate shear adhesion strength (a) before the heat cycle test.

(Gelling Time)

The gelling time was measured according to the JACT test method RS-5 and JIS K-6910-1995. Specifically, by using as a sample each of the epoxy resin compositions prepared according to Table 3, the gelling time was measured with a gelation tester. The sample was heated under stirring on a hot plate at 170° C., and the time elapsed until no sticky threads were formed between the sample and the stirring rod was taken as the gelling time.

(Water Absorption Rate Test)

The water absorption rate was measured according to JIS K7209.

(Glycidylation Ratio)

The glycidylation ratio was calculated on the basis of the following formula:

Glycidylation ratio(%)=$Et/Ea$×100(%)

Et=Theoretical epoxy equivalent (g/eq.)
Ea=Measured epoxy equivalent (g/eq.)

The theoretical epoxy equivalent (Et) was determined from the molecular weight obtained from the structural formula glycidylated to 100%.

The measured epoxy equivalent (Ea) was determined as described above according to JIS K7236.

(Impact Test)

Each of the epoxy resin compositions prepared according to Table 2 was cast into a 100 mm×100 mm×2 mm fluororesin plate mold, and cured at 180° C. for 2 hours to yield a cured product. The obtained cured products were subjected to an impact test with the Du Pont impact tester HSO. On each of the cured products, one end of an impact shaft of 3.1 mm in radius was placed, a weight was dropped on the impact shaft, whether or not the cured product was cracked was determined, and the evaluation was performed on the basis of the following standards.

X: When the cured product was cracked, the product of the weight (kg)×the height (cm) was less than 3.

Δ: When the cured product was cracked, the product of the weight (kg)×the height (cm) was 3 or more and less than 7.

◯: When the cured product was cracked, the product of the weight (kg) x the height (cm) was 7 or more less than 20.

◎: When the cured product was cracked, the product of the weight (kg) x the height (cm) was 20 or more.

(Adhesiveness to Silver Plating)

By using the silver plated standard specimen C1100P (manufactured by Nippon Testpanel Co., Ltd.), 10 pieces of samples were prepared in the same manner as in the item of "copper plate shear adhesion strength" (based on JIS K6850). Of the samples, 5 pieces of the samples were subjected to the measurement of "the adhesion strength a to the silver plating before the moisture absorption test." The adhesion strength a was taken as the arithmetic average value of the measured values of the five pieces of the samples.

The other five pieces of the samples were allowed to stand still in a constant-temperature and constant-humidity chamber set at 85° C. and 85 RH % for 300 hours and allowed to absorb moisture. The samples after the moisture absorption were subjected to the measurement of "the adhesion strength b to the silver plating after the moisture absorption test" in the same manner as in the measurement method of "the adhesion strength a to the silver plating before the moisture absorption test." The adhesion strength b was taken as the arithmetic average value of the measured values of the 5 pieces of the samples after the absorption of moisture.

The ratio of the adhesion strength b to the adhesion strength a was taken as the adhesion strength retention rate (b/a).

(Penetration Test)

On a glass plate, two pieces of 20-micron thick fluororesin seals were placed with spacing of 30 mm, and were sandwiched between the glass plate and another glass plate. The resulting laminate was horizontally placed on a hot plate set at 150° C., and when the temperature of the upper side glass plate reached 145° C., the epoxy resin composition was dropped into between the two glass plates and retained for 15 minutes. Then, the distance over which the epoxy resin composition penetrated was measured. The evaluation was performed on the basis of the following standards.

◎: The penetration distance was 30 to 100 mm, and the epoxy resin composition was uniformly cured.

◯: The penetration distance was 15 to 30 mm, and the epoxy resin composition was uniformly cured.

Δ: The penetration distance was 30 to 100 mm, and the cured product underwent the occurrence of turbidity or unevenness.

X: The penetration distance was 15 mm or less, or alternatively the epoxy resin composition was not cured and penetrated over the distance of 100 mm or more.

(Cured Product Drop Test)

A semiconductor device produced with the below-described method was dropped in a horizontal attitude 10 times from the height of 100 cm from a concrete surface. The occurrence or non-occurrence of the detachment of the epoxy resin in the semiconductor device was examined. The occurrence or non-occurrence was verified with an ultrasonic flaw detector (Type: mi-scope hyper, manufactured by Hitachi Construction Machinery Co., Ltd.). The evaluation of the cured product drop test was performed on the basis of the following standards.

◎: No detachment occurred even when the semiconductor device was dropped 10 times.

◯: The detachment occurred at the sixth to ninth drop.

Δ: The detachment occurred at the second to fifth drop.

X: The detachment occurred at the first drop.

(Reflow Resistance)

A semiconductor device produced with the below-described method was subjected to a moisture absorption treatment of a JEDEC moisture resistance level of 3 (treatment at 30° C., relative humidity of 60%, and treatment time of 168 hours), and then subjected three times to an IR reflow treatment (peak temperature: 260° C., treatment time: 60 seconds). Then, the occurrence or non-occurrence of the detachment of the epoxy resin composition inside the semiconductor device was examined. The occurrence or non-occurrence of the detachment was verified with a supersonic flaw detector (Model mi-scope hyper, manufactured by Hitachi Construction Machinery Co., Ltd.). The evaluation of the reflow resistance was performed with the following standards.

◯: No detachment was observed.

X: Detachment was observed.

(Thermal Cycle Resistance)

A semiconductor device produced with the below-described method was subjected to 1000 cycles of a thermal cycle treatment in one cycle of which the semiconductor device was maintained at −55° C. for 30 minutes, successively increased in temperature to 125° C. over 20 minutes, and further maintained at 125° C. for 30 minutes. In the course of the thermal cycle treatment, at every 250 cycles, the occurrence or non-occurrence of the detachment in the interface between the semiconductor chip and the epoxy resin composition inside the semiconductor device was examined. The occurrence or non-occurrence of the interfacial detachment was verified with a supersonic flaw detector (Model mi-scope hyper, manufactured by Hitachi Construction Machinery Co., Ltd.). The evaluation of the thermal cycle resistance was performed on the basis of the following standards.

⊚: No detachment was observed even when 1000 cycles were performed.

○: Detachment was observed when 750 cycles were performed.

Δ: Detachment was observed when 500 cycles were performed.

X: Detachment was observed when 250 cycles were performed.

Example 1

Glycidylation Reaction

In a flask equipped with a thermometer, a dropping funnel, a condenser and a stirrer, 270 g (hydroxyl group: 1 equivalent) of the dialcohol obtained by addition reaction of 5 moles of propylene oxide with 1 mole of bisphenol A, 463 g (5.00 moles) of epichlorohydrin and a 50% by mass tetramethylammonium chloride aqueous solution (10 g) were mixed, and heated under reduced pressure to be refluxed at 60 to 65° C. Then, to the reaction mixture, 400 g of a 50% by mass sodium hydroxide aqueous solution was added dropwise over 2 hours. At the time of dropwise addition, water was continuously removed as an azeotropic mixture with epichlorohydrin, and at the same time, only the condensed epichlorohydrin layer was continuously returned to the reactor. After the completion of the dropwise addition, the reaction mixture was allowed to react for further 2 hours, and then the mixture was cooled and washed with water repeatedly to remove the by-produced sodium chloride. The excessive epichlorohydrin was distilled to be removed under reduced pressure, and thus, a crude resin composition was obtained.

(Low Chlorination Reaction)

In 200 g of methyl isobutyl ketone, 100 g of the obtained crude resin composition was dissolved, 0.22 g of a 50% by mass sodium hydroxide aqueous solution was added to the resulting solution, and the mixture was allowed to react at 80° C. for 2 hours. After the completion of the reaction, methyl isobutyl ketone was removed by washing with water, to yield the epoxy resin composition A.

Figure 2:
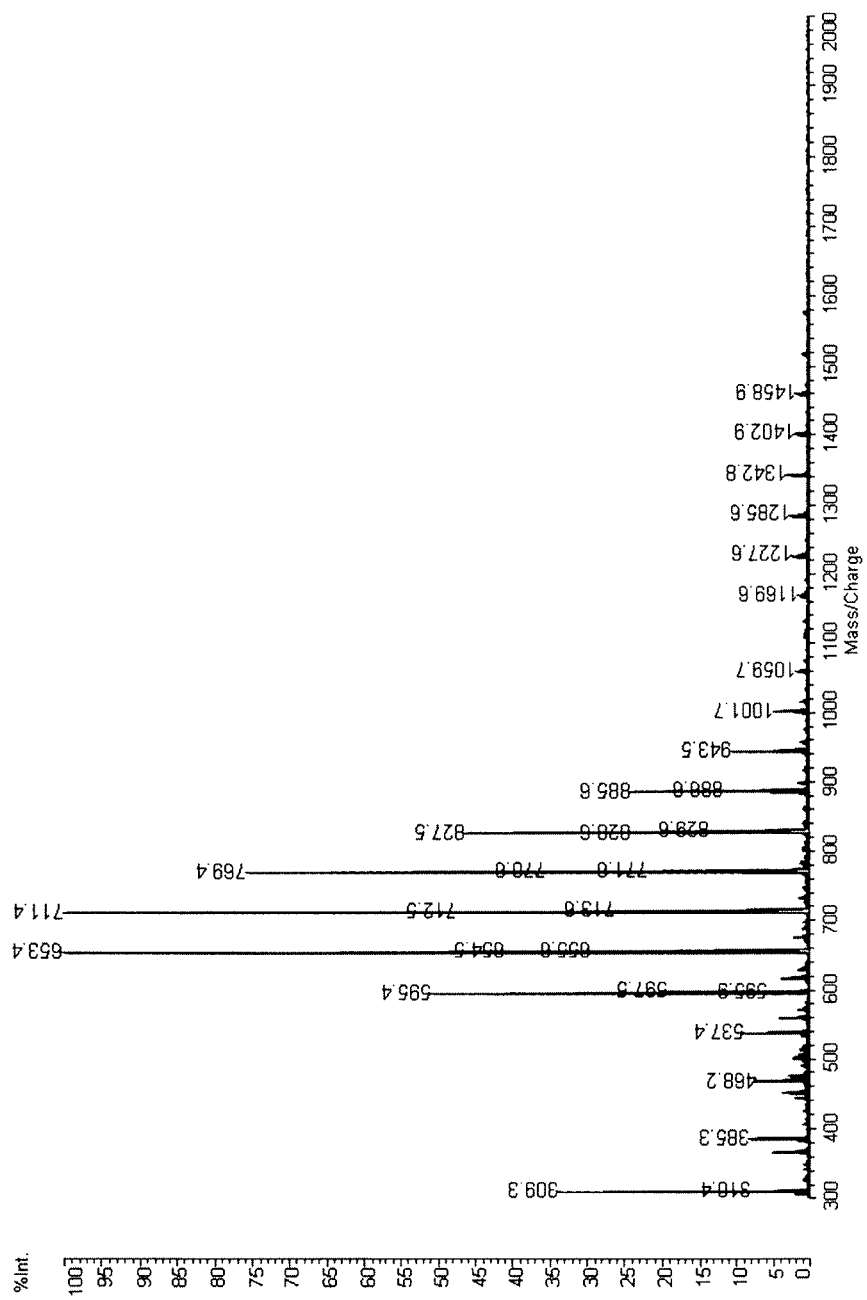
FIG. 2 shows the MALDI-MS chart of the epoxy resin composition A prepared in Example 1.

As an example, FIG. 1 shows the NMR chart of the epoxy resin composition A obtained in Example 1, and FIG. 2 shows the MALDI-MS chart of the epoxy resin composition A obtained in Example 1. When the epoxy resin composition A was analyzed, based on 100 parts by mass of the epoxy resin a1 having the structure represented by formula (1), the epoxy resin a2 having the structure represented by formula (2) was found to be included in an amount of 1.3 parts by mass.

It was verified that in the epoxy resin a1, $R^1$ was a propylene group, $R^2$ was a divalent group derived from bisphenol A, $G^1$ was a glycidyl group, and 74 mol % of $G^2$ was a glycidyl group and 26 mol % of $G^2$ was hydrogen. The range of m and n of formula (1) was such that $6≤(m+n)≤12$. In the epoxy resin a1, the proportion of the component (component a) in which m and n in formula (1) satisfied the relation $6≤(m+n)≤12$ was found to be 48 mol %.

It was verified that in the epoxy resin a2, $R^1$ was an isopropylene group, $R^2$ was a divalent group derived from bisphenol A, $G^1$ was a glycidyl group, and $G^2$ was a glycidyl group. It was verified that m, n, m' and n' of formula (2) satisfied the relation $6≤(m+n+m'+n')≤15$.

In the epoxy resin A, the epoxy equivalent was 371 g/eq., the viscosity at 25° C. was 952 mPa·s, the total chlorine content was 512 ppm, and the hydrolytic chlorine content was 56 ppm.

Example 2

With respect to the dialcohol used in Example 1, the dialcohol was altered from "the dialcohol obtained by addition reaction of 5 moles of propylene oxide with 1 mole of bisphenol A," to "the dialcohol obtained by addition reaction of 2 moles of epoxypentane with 1 mole of biphenol." Under the same conditions as in Example 1 except for the above-described alteration of the dialcohol, the epoxy resin composition B was obtained.

When the obtained epoxy resin composition B was analyzed, based on 100 parts by mass of the epoxy resin b1 having the structure represented by formula (1), the epoxy resin b2 having the structure represented by formula (2) was found to be included in an amount of 2.5 parts by mass.

It was verified that in the epoxy resin b1, $R^1$ was a pentyl group ($-CHCH(C_3H_7)-$), $R^2$ was a biphenyl group, $G^1$ was a glycidyl group, and 99.5 mol % of $G^2$ was a glycidyl group and 0.5 mol % of $G^2$ was hydrogen. In the epoxy resin b1, the range of m and n of formula (1) was such that $1≤(m+n)≤9$. In the epoxy resin b1, the proportion of the component (component a) in which m and n in formula (1) satisfied the relation $6≤(m+n)≤12$ was found to be 18 mol %.

It was verified that in the epoxy resin b2, $R^1$ was a pentyl group, $R^2$ was a biphenyl group, $G^1$ was a glycidyl group, and $G^2$ was a glycidyl group. It was verified that m, n, m' and n' of formula (2) satisfied the relation $2≤(m+n+m'+n')≤13$.

In the epoxy resin B, the epoxy equivalent was 262 g/eq., the viscosity at 25° C. was 1782 mPa·s, the total chlorine content was 423 ppm, and the hydrolytic chlorine content was 50 ppm.

Example 3

In a reactor, 270 g of the epoxy resin composition A produced in Example 1 was placed, and 1.8 g of boron trifluoride-diethyl ether complex as a catalyst was placed, then the resulting mixture was heated to 60° C., and 36 g of phenyl glycidyl ether ("EX141," epoxy equivalent: 150 g/eq., manufactured by Nagase ChemteX Corp.) was added dropwise to the mixture over 1 hour. After the completion of the dropwise addition, the mixture was allowed to react at 60° C. for 1.5 hours, 6.0 g of a 50% by mass sodium hydroxide aqueous solution was added to deactivate the boron trifluoride-diethyl ether, and then the catalyst residue was removed with 300 g of purified water to yield 291 g of a crude resin composition.

The epoxy resin composition C was obtained by performing the operations in the same manner as in Example 1 except that 270 g of the obtained crude resin composition was used in place of "the dialcohol obtained by addition reaction of 5 moles of propylene oxide with 1 mole of bisphenol A" in Example 1.

When the obtained epoxy resin composition C was analyzed, based on 100 parts by mass of the epoxy resin c1 having the structure represented by formula (1), the epoxy resin c2 having the structure represented by formula (2) was found to be included in an amount of 1.2 parts by mass.

It was verified that in the epoxy resin c1, $R^1$ was an isopropylene group or a phenoxyisopropylene group ($-CH_2CH(CH_2OC_6H_6)-$), $R^2$ was a divalent group derived from bisphenol A, $G^1$ was a glycidyl group, and 71.8 mol % of $G^2$ was a glycidyl group and 28.2 mol % of $G^2$ was a hydrogen atom. In the epoxy resin c1, the range of m and n of formula (1) was such that $3≤(m+n)≤12$. In the epoxy resin c1, the proportion of the component (component a) in which m and n in formula (1) satisfied the relation 6≤(m+n)≤12 was found to be 48 mol %.

It was verified that in the epoxy resin c2, 86 mol % of $R^1$ was an isoprene group and 14 mol % of $R^1$ was a phenoxyisoprene group, $R^2$ was a phenoxyisoprene group, $G^1$ was a glycidyl group, and $G^2$ was a glycidyl group. It was verified that m, n, m' and n' of formula (2) satisfied the relation 6≤(m+n+m'+n') 15.

In the epoxy resin composition C, the epoxy equivalent was 385 g/eq., the viscosity at 25° C. was 1245 mPa·s, the total chlorine content was 621 ppm, and the hydrolytic chlorine content was 57 ppm.

Example 4

In a flask equipped with a thermometer and a stirrer, 120 g of resorcinol and 172 g of triethylene glycol divinyl ether were placed, and the resulting mixture was increased in temperature to 120° C. over 1 hour. Then, the mixture was allowed to react at 120° C. for 6 hours to yield 290 g of transparent semi-solid modified polyhydric phenols. In a reactor, 290 g of the obtained modified polyhydric phenols, 735 g of epichlorohydrin and 185 g of n-butanol were placed and dissolved. Then, by heating under reduced pressure, the resulting mixture was refluxed at 60 to 65° C. To the reaction mixture, 130.3 g of a 50% by mass sodium hydroxide aqueous solution was added dropwise over 2 hours. At the time of dropwise addition, water was continuously removed as an azeotropic mixture with epichlorohydrin, and at the same time, only the condensed epichlorohydrin layer was continuously returned to the reactor. Then, the reaction mixture was allowed to react for further 2 hours, and then the mixture was cooled and was washed with water repeatedly to remove the by-produced sodium chloride. The excessive epichlorohydrin was distilled to be removed under reduced pressure, and thus, a crude resin was obtained.

In 200 g of methyl isobutyl ketone, 100 g of the obtained crude resin was dissolved, 0.22 g of a 50% by mass sodium hydroxide aqueous solution was added to the resulting solution, and the mixture was allowed to react at 80° C. for 2 hours; then, methyl isobutyl ketone was removed by washing with water, to yield the epoxy resin D.

When the obtained epoxy resin D was analyzed, the epoxy resin D was verified to be an epoxy resin in which the structure was represented by formula (1), $R^1$ was a phenylene group, $R^2$ was a triethylene group, $G^1$ was a glycidyl group, and $G^2$ was a glycidyl group. In the epoxy resin D, m and n of formula (1) were 1. In the epoxy resin D, the proportion of the component (component a) in which m and n in formula (1) satisfied the relation 6≤(m+n)≤12 was found to be 0 mol %.

In the epoxy resin D, the epoxy equivalent was 286 g/eq., the viscosity at 25° C. was 12000 mPa·s, the total chlorine content was 877 ppm, and the hydrolytic chlorine content was 72 ppm.

Example 5

The epoxy resin composition E was obtained in the same manner as in Example 1 except that in the glycidylation reaction, the reaction time after the dropwise addition of the 50% by mass sodium hydroxide aqueous solution was altered to 8 hours.

When the obtained epoxy resin composition E was analyzed, based on 100 parts by mass of the epoxy resin e1 having the structure represented by formula (1), the epoxy resin e2 having the structure represented by formula (2) was found to be included in an amount of 2.4 parts by mass.

It was verified that in the epoxy resin e1, $R^1$ was an isopropylene group, $R^2$ was a divalent group derived from bisphenol A, $G^1$ was a glycidyl group, and 80 mol % of $G^2$ was a glycidyl group and 20 mol % of $G^2$ was hydrogen. In the epoxy resin e1, the range of m and n of formula (1) was such that 3≤(m+n)≤12. In the epoxy resin e1, the proportion of the component (component a) in which m and n in formula (1) satisfied the relation 6≤(m+n)≤12 was found to be 67 mol %.

It was verified that in the epoxy resin e2, $R^1$ was an isoprene group, $R^2$ was a divalent group derived from bisphenol A, $G^1$ was a glycidyl group, and $G^2$ was a glycidyl group. It was verified that m, n, m' and n' of formula (2) satisfied the relation 6≤(m+n+m'+n')≤15.

In the epoxy resin composition E, the epoxy equivalent was 420 g/eq., the viscosity at 25° C. was 1481 mPa·s, the total chlorine content was 1273 ppm, and the hydrolytic chlorine content was 366 ppm.

Example 6

The epoxy resin composition F was obtained in the same manner as in Example 1 except that in the glycidylation reaction, the 50% by mass tetramethylammonium chloride aqueous solution was not added.

When the obtained epoxy resin composition F was analyzed, based on 100 parts by mass of the epoxy resin f1 having the structure represented by formula (1), the epoxy resin f2 having the structure represented by formula (2) was found to be included in an amount of 0.5 part by mass.

It was verified that in the epoxy resin f1, $R^1$ was an isopropylene group, $R^2$ was a divalent group derived from bisphenol A, $G^1$ was a glycidyl group, and 62 mol % of $G^2$ was a glycidyl group and 38 mol % of $G^2$ was hydrogen. In the epoxy resin f1, the range of m and n of formula (1) was such that 3≤(m+n)≤12. In the epoxy resin f1, the proportion of the component (component a) in which m and n in formula (1) satisfied the relation 6≤(m+n)≤12 was found to be 35 mol %.

It was verified that in the epoxy resin f2, $R^1$ was an isopropylene group, $R^2$ was a divalent group derived from bisphenol A, $G^1$ was a glycidyl group, and $G^2$ was a glycidyl group. It was verified that m, n, m' and n' of formula (2) satisfied the relation 6≤(m+n+m'+n')≤14.

In the epoxy resin composition F, the epoxy equivalent was 332 g/eq., the viscosity at 25° C. was 1213 mPa·s, the total chlorine content was 530 ppm, and the hydrolytic chlorine content was 242 ppm.

Example 7

The epoxy resin composition G was obtained in the same manner as in Example 1 except that in the glycidylation reaction, 640 g of a 50% by mass potassium hydroxide aqueous solution was used in place of 400 g of the 50% by mass sodium hydroxide aqueous solution.

When the obtained epoxy resin composition G was analyzed, based on 100 parts by mass of the epoxy resin g1 having the structure represented by formula (1), the epoxy resin g2 having the structure represented by formula (2) was found to be included in an amount of 5.4 parts by mass.

It was verified that in the epoxy resin g1, $R^1$ was an isopropylene group, $R^2$ was a divalent group derived from bisphenol A, $G^1$ was a glycidyl group, and 81 mol % of $G^2$ was a glycidyl group and 19 mol % of $G^2$ was hydrogen. In the epoxy resin g1, the range of m and n of formula (1) was such that 3≤(m+n)≤12. In the epoxy resin g1, the proportion of the component (component a) in which m and n in formula (1) satisfied the relation 6≤(m+n)≤12 was found to be 76 mol %.

It was verified that in the epoxy resin g2, $R^1$ was an isopropylene group, $R^2$ was a divalent group derived from bisphenol A, $G^1$ was a glycidyl group, and $G^2$ was a glycidyl group. It was verified that m, n, m' and n' of formula (2) satisfied the relation 6≤(m+n+m'+n')≤18.

In the epoxy resin composition G, the epoxy equivalent was 495 g/eq., the viscosity at 25° C. was 2093 mPa·s, the total chlorine content was 2883 ppm, and the hydrolytic chlorine content was 657 ppm.

Example 8

The epoxy resin composition H was obtained in the same manner as in Example 1 except that the dialcohol was altered from "the dialcohol obtained by addition reaction of 5 moles of propylene oxide with 1 mole of bisphenol A," to "the dialcohol obtained by addition reaction of 3 moles of propylene oxide with 1 mole of bisphenol A."

When the obtained epoxy resin composition H was analyzed, based on 100 parts by mass of the epoxy resin h1 having the structure represented by formula (1), the epoxy resin h2 having the structure represented by formula (2) was found to be included in an amount of 1.4 parts by mass.

It was verified that in the epoxy resin h1, $R^1$ was an isopropylene group, $R^2$ was a divalent group derived from bisphenol A, $G^1$ was a glycidyl group, and 90 mol % of $G^2$ was a glycidyl group and 10 mol % of $G^2$ was hydrogen. In the epoxy resin h1, the range of m and n of formula (1) was such that 1≤(m+n)≤10. In the epoxy resin h1, the proportion of the component (component a) in which m and n in formula (1) satisfied the relation 6≤(m+n)≤12 was found to be 22 mol %.

It was verified that in the epoxy resin h2, $R^1$ was an isopropylene group, $R^2$ was a divalent group derived from bisphenol A, $G^1$ was a glycidyl group, and $G^2$ was a glycidyl group. It was verified that m, n, m' and n' of formula (2) satisfied the relation 2≤(m+n+m'+n')≤12.

In the epoxy resin composition H, the epoxy equivalent was 309 g/eq., the viscosity at 25° C. was 1565 mPa·s, the total chlorine content was 499 ppm, and the hydrolytic chlorine content was 50 ppm.

Example 9

Glycidylation Reaction

In a flask equipped with a thermometer, a dropping funnel, a condenser and a stirrer, 270 g (hydroxyl group: 1 equivalent) of the dialcohol obtained by addition reaction of 5 moles of propylene oxide with 1 mole of bisphenol A, 185 g (2.00 moles) of epichlorohydrin and a 50% by mass tetramethylammonium chloride aqueous solution (10 g) were mixed, and heated under reduced pressure to be refluxed at 60 to 65° C. Then, to the reaction mixture, 80 g of a 50% by mass sodium hydroxide aqueous solution was added dropwise over 2 hours. At the time of dropwise addition, water was continuously removed as an azeotropic mixture with epichlorohydrin, and at the same time, only the condensed epichlorohydrin layer was continuously returned to the reactor. After the completion of the dropwise addition, 370 g of epichlorohydrin was placed in the reactor at once, and then, 320 g of a 50% by mass sodium hydroxide aqueous solution was added dropwise to the reaction mixture. After the completion of the dropwise addition, the reaction mixture was allowed to react for further 2 hours, and then the mixture was cooled and was washed with water repeatedly to remove the by-produced sodium chloride. The excessive epichlorohydrin was distilled to be removed under reduced pressure, and thus, a crude resin composition was obtained.

(Low Chlorination Reaction)

In 200 g of methyl isobutyl ketone, 100 g of the obtained crude resin composition was dissolved, 0.22 g of a 50% by mass sodium hydroxide aqueous solution was added to the resulting solution, and the mixture was allowed to react at 80° C. for 2 hours. After the completion of the reaction, methyl isobutyl ketone was removed by washing with water, to yield the epoxy resin composition I.

When the obtained epoxy resin composition I was analyzed, based on 100 parts by mass of the epoxy resin i1 having the structure represented by formula (1), the epoxy resin i2 having the structure represented by formula (2) was found to be included in an amount of 12.1 parts by mass.

It was verified that in the epoxy resin i1, $R^1$ was an isopropylene group, $R^2$ was a divalent group derived from bisphenol A, $G^1$ was a glycidyl group, and 87 mol % of $G^2$ was a glycidyl group and 13 mol % of $G^2$ was hydrogen. In the epoxy resin i1, the range of m and n of formula (1) was such that 3≤(m+n)≤12. In the epoxy resin i1, the proportion of the component (component a) in which m and n in formula (1) satisfied the relation 6≤(m+n)≤12 was found to be 56 mol %.

It was verified that in the epoxy resin i2, $R^1$ was an isopropylene group, $R^2$ was a divalent group derived from bisphenol A, $G^1$ was a glycidyl group, and $G^2$ was a glycidyl group. It was verified that m, n, m' and n' of formula (2) satisfied the relation 6≤(m+n+m'+n')≤20.

In the epoxy resin composition I, the epoxy equivalent was 335 g/eq., the viscosity at 25° C. was 8052 mPa·s, the total chlorine content was 612 ppm, and the hydrolytic chlorine content was 56 ppm.

Example 10

The epoxy resin composition J was obtained in the same manner as in Example 1 except that the condensed epichlorohydrin was not collected but was all returned to the reactor.

When the obtained epoxy resin composition J was analyzed, based on 100 parts by mass of the epoxy resin j1 having the structure represented by formula (1), the epoxy resin j2 having the structure represented by formula (2) was found to be included in an amount of 0.05 part by mass.

It was verified that in the epoxy resin j1, $R^1$ was an isopropylene group, $R^2$ was a divalent group derived from bisphenol A, $G^1$ was a glycidyl group, and 82 mol % of $G^2$ was a glycidyl group and 18 mol % of $G^2$ was hydrogen. In the epoxy resin j1, the range of m and n of formula (1) was such that 3≤(m+n)≤12. In the epoxy resin j1, the proportion of the component (component a) in which m and n in formula (1) satisfied the relation 6≤(m+n)≤12 was found to be 59 mol %.

It was verified that in the epoxy resin j2, $R^1$ was an isopropylene group, $R^2$ was a divalent group derived from bisphenol A, $G^1$ was a glycidyl group, and $G^2$ was a glycidyl group. It was verified that m, n, m' and n' of formula (2) satisfied the relation 6≤(m+n+m'+n')≤15.

The epoxy equivalent was 385 g/eq., the viscosity at 25° C. was 1020 mPa·s, the total chlorine content was 486 ppm, and the hydrolytic chlorine content was 47 ppm.

Comparative Example 1

Glycidylation Reaction

In a flask equipped with a thermometer, a dropping funnel, a condenser and a stirrer, 425 g of a solid bisphenol A-based epoxy resin ("AER6061", epoxy equivalent: 425 g/eq., manufactured by Asahi Kasei E-Materials Corp.), 463 g of epichlorohydrin (5.00 moles) were mixed and they are dissolved at room temperature. Then, a 50% by mass tetramethylammonium chloride aqueous solution (10 g) was mixed with the resulting solution, the resulting mixture was continuously heated to increase the temperature, and then heated under reduced pressure to be refluxed at 60 to 65° C. Then, 80 g of a 50% by mass sodium hydroxide aqueous solution was added dropwise to the reaction mixture over 2 hours. At the time of dropwise addition, water was continuously removed as an azeotropic mixture with epichlorohydrin, and at the same time, only the condensed epichlorohydrin layer was continuously returned to the reactor. After the dropwise addition, the reaction mixture was allowed to react for further 2 hours, and then the mixture was cooled and was washed with water repeatedly to remove the by-produced sodium chloride. The excessive epichlorohydrin was distilled to be removed under reduced pressure, and thus, the resin K was obtained.

When the obtained epoxy resin K was analyzed, it was verified that the epoxy resin did not at least correspond to the structures represented by formula (1) and formula (2).

In the epoxy resin K, the epoxy equivalent was 392 g/eq., the viscosity at 25° C. was 1400000 mPa·s, the total chlorine content was 1512 ppm, and the hydrolytic chlorine content was 253 ppm.

The measurement results of the physical properties of Examples 1 to 10 and Comparative Examples 1 and 2 are shown in Tables 1 and 2.

Examples 11 to 21 and Comparative Examples 3 to 8

The epoxy resin compositions of Examples 1 to 3 and 5 to 10, and Comparative Examples 1 and 2, and the epoxy resin of Example 4 were mixed with the materials listed in Tables 3 and 4, under the conditions described in Tables 3 and 4, and thus epoxy resin compositions were prepared. It is to be noted that in Example 11, the epoxy resin composition A was used alone.

To the obtained epoxy resin compositions, diaminodiphenylmethane epoxy was added (see Tables 3 and 4) in a proportion that the amount of active hydrogen (>NH) was 1 equivalent based on 1 equivalent of epoxy group, and then the resulting mixtures were cured under the conditions of 180° C. and 2 hours to yield epoxy resin cured products. The epoxy resin cured products were subjected to the evaluations shown in Tables 3 and 4.

Examples 22 to 31 and Comparative Examples 9 to 13

Individual materials were mixed under the conditions described in Tables 5 and 6 to prepare epoxy resin compositions. The obtained epoxy resin compositions were used as the sealing epoxy resin compositions to produce semiconductor devices.

(Production of Semiconductor Devices)

Figure 3:
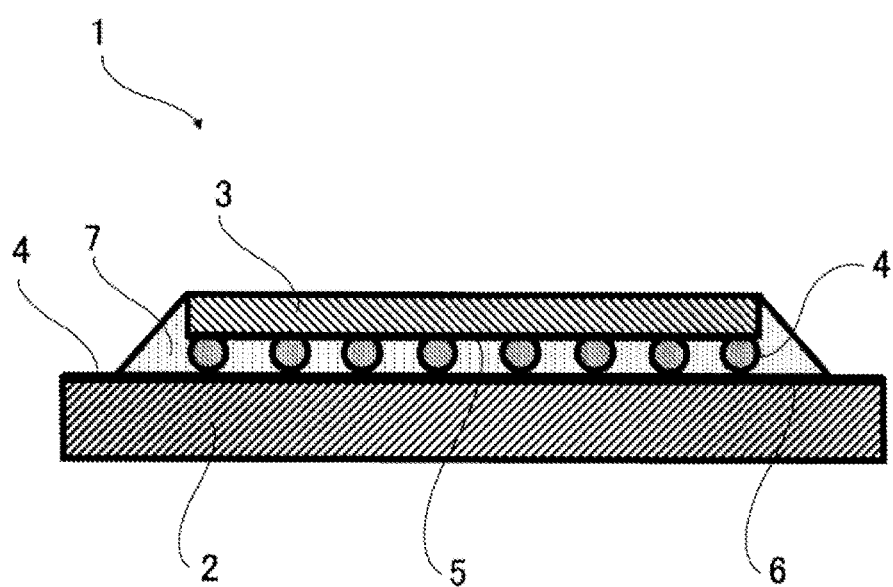
FIG. 3 shows a schematic cross-sectional view of the semiconductor devices with a semiconductor chip mounted thereon, prepared in Examples of the present invention.

The sealing epoxy resin compositions of Examples 22 to 31 and Comparative Examples 9 to 13 were each used to prepare the semiconductor device 1 shown in FIG. 3. FIG. 3 shows a schematic cross-sectional view of the semiconductor devices 1 with a semiconductor chip 3 mounted thereon, prepared in Examples of the present invention. A semiconductor chip mounted substrate was prepared in which a substrate 2 ("ELC4782" manufactured by Sumitomo Bakelite Co., Ltd.) and a semiconductor chip 3 ("BGA377" manufactured by Panasonic Corp.) were beforehand flip-chip connected with solder bumps 4 ("MUL α-S" manufactured by Mitsubishi Material Corp., Composition of solder bump 4: Sn/Ag/Cu). The size of the semiconductor chip 3 was 10 mm×10 mm×0.2 mm, and the size of the substrate was 20 mm×20 mm×0.4 mm. The substrate 2 and the semiconductor chip 3 were connected with 176 bumps 4 peripherally (a form in which bumps were located only in the periphery), and the height of the bumps 4 was 0.08 mm and the pitch interval was 0.04 mm. Silicon nitride (SiN) was used for the circuit protection film 5 of the semiconductor chip 3, and "AUS308" manufactured by Taiyo Ink Mfg. Co., Ltd. was used for the solder resist 6 on the substrate 2.

Plasma treatment was performed before a sealing epoxy resin composition 7 was filled on the substrate 2 with the semiconductor chip 3 mounted thereon. As a plasma apparatus, the "AP-1000" manufactured by March Plasma Systems, Inc. was used. The treatment conditions were as follows.

Gas type: Ar
Gas flow rate: 50 mL/m
Treatment intensity: 350 W
Treatment time: 420 seconds
Direct plasma mode After the plasma treatment, the above-described substrate 2 with the semiconductor chip 3 mounted thereon was heated on a hot plate set at 110° C., the epoxy resin composition 7 was dispensed in an amount of 12 mg on one side of the semiconductor chip 3 so as to fill the inside of the gap between the substrate and the semiconductor chip 3, then the substrate 2 with the semiconductor chip 3 was maintained in an oven set at 150° C. for 120 minutes so as to thermally cure the sealing epoxy resin composition 7, and thus a semiconductor device 1 was obtained. The obtained sealing epoxy resin compositions 7, the cured products thereof and the semiconductor devices 1 were evaluated. The respective evaluation results are shown in Tables 5 and 6 presented below.

TABLE 1

|  |  | Example 1 | Example 2 | Example 3 | Example 4 | Example 5 | Example 6 | Example 7 |
|---|---|---|---|---|---|---|---|---|
| Epoxy resin composition/epoxy resin |  | A | B | C | D | E | F | G |
| Glycidylation ratio | mol % | 74 | 99.5 | 71.8 | 100 | 80 | 62 | 81 |
| Proportion (6 ≤ m + n ≤ 12) | mol % | 48 | 18 | 48 | 0 | 67 | 35 | 76 |

TABLE 1-continued

|  |  | Example 1 | Example 2 | Example 3 | Example 4 | Example 5 | Example 6 | Example 7 |
|---|---|---|---|---|---|---|---|---|
| Epoxy equivalent | g/eq. | 371 | 262 | 385 | 286 | 420 | 332 | 495 |
| Viscosity | mPa·s | 952 | 1782 | 1245 | 12000 | 1481 | 1213 | 2093 |
| Total chlorine content | ppm | 512 | 423 | 621 | 877 | 1273 | 530 | 2883 |
| Amount of component of formula (2) based on 100 parts by mass of component of formula (1) | parts by mass | 1.3 | 2.5 | 1.2 | 0 | 2.4 | 0.5 | 5.4 |
| Evaluation of compatibility |  | ○ | ○ | ○ | ○ | ○ | ○ | x |

TABLE 2

|  |  | Example 8 | Example 9 | Example 10 | Comparative Example 1 | Comparative Example 2 |
|---|---|---|---|---|---|---|
| Epoxy resin composition/epoxy resin |  | H | I | J | K | Epolite 40E |
| Glycidylation ratio | mol % | 90 | 87 | 82 | 100 | 96 |
| Proportion ($6 \leq m + n \leq 12$) | mol % | 22 | 56 | 59 | 0 | 0 |
| Epoxy equivalent | g/eq. | 309 | 335 | 385 | 392 | 135 |
| Viscosity | mPa·s | 1565 | 8052 | 1020 | 1400000 | 40 |
| Total chlorine content | ppm | 499 | 612 | 486 | 1512 | 18220 |
| Amount of component of formula (2) based on 100 parts by mass of component of formula (1) | parts by mass | 1.4 | 12.1 | 0.05 | 0 | 0 |
| Evaluation of compatibility |  | Δ | ○ | ○ | ○ | x |

TABLE 3

|  |  |  | Example |  |  |  |  |  |  |  |  |  |  |
|---|---|---|---|---|---|---|---|---|---|---|---|---|---|
|  |  |  | 11 | 12 | 13 | 14 | 15 | 16 | 17 | 18 | 19 | 20 | 21 |
| Composition | Epoxy resin composition A | parts by mass | 100 | 50 |  |  |  |  |  |  |  |  |  |
|  | Epoxy resin composition B |  |  |  | 50 |  |  |  |  |  |  |  |  |
|  | Epoxy resin composition C |  |  |  |  | 50 |  |  |  |  |  |  |  |
|  | Epoxy resin D |  |  |  |  |  | 10 |  |  |  |  |  |  |
|  | Epoxy resin composition E |  |  |  |  |  |  | 50 |  |  |  |  |  |
|  | Epoxy resin composition F |  |  |  |  |  |  |  | 80 |  |  |  |  |
|  | Epoxy resin composition G |  |  |  |  |  |  |  |  | 20 |  |  |  |
|  | Epoxy resin composition H |  |  |  |  |  |  |  |  |  | 50 |  |  |
|  | Epoxy resin composition I |  |  |  |  |  |  |  |  |  |  | 50 |  |
|  | Epoxy resin composition J |  |  |  |  |  |  |  |  |  |  |  | 50 |
|  | Epoxy resin composition K |  |  |  |  |  |  |  |  |  |  |  |  |
|  | Epolite 40E |  |  |  |  |  |  |  |  |  |  |  |  |
|  | YED216 |  |  |  |  |  |  |  |  |  |  |  |  |
|  | AER260 |  |  |  |  |  |  |  |  |  |  |  |  |
|  | AER6011 |  |  |  |  |  |  |  |  |  |  |  |  |
|  | YL983U |  |  | 50 | 50 | 50 | 90 | 50 | 20 | 80 | 50 | 50 | 50 |
|  | Diaminodiphenyl-methane |  | 13.4 | 22.7 | 25.5 | 22.5 | 29.4 | 21.9 | 19.2 | 26.8 | 24.0 | 23.4 | 22.5 |
| Measurement results | Tg | °C. | 15 | 101 | 141 | 98 | 132 | 88 | 48 | 132 | 123 | 118 | 85 |
|  | Storage modulus at 30° C. | MPa | 35 | 1352 | 1572 | 1240 | 2147 | 1206 | 873 | 1762 | 2083 | 2158 | 1209 |
|  | Elastic modulus at (Tg − 20) °C. | MPa | 450 | 872 | 1347 | 782 | 1752 | 798 | 898 | 982 | 1782 | 1942 | 982 |
|  | Elastic modulus at (Tg + 20) °C. | MPa | 8.6 | 11.5 | 21.5 | 9.7 | 85.2 | 10.8 | 38.4 | 27.3 | 38.5 | 72.2 | 31.7 |
|  | E'/(273 + Tg/3) |  |  | 0.1 | 4.4 | 4.9 | 4.1 | 6.8 | 4.0 | 3.0 | 5.6 | 6.6 | 6.9 | 4.0 |
|  | E'(Tg − 20)/E'(Tg + 20) |  |  | 52.3 | 75.8 | 62.7 | 80.6 | 20.6 | 73.9 | 23.4 | 36.0 | 46.3 | 26.9 | 31.0 |

TABLE 3-continued

|  |  | Example | | | | | | | | | | |
|---|---|---|---|---|---|---|---|---|---|---|---|---|
|  |  | 11 | 12 | 13 | 14 | 15 | 16 | 17 | 18 | 19 | 20 | 21 |
| Bending strength | MPa | — | 320 | 338 | 306 | 329 | 340 | 309 | 342 | 353 | 387 | 294 |
| Fracture toughness ($K_{Ic}$) | MPa/m$^{0.5}$ | — | 1.52 | 1.42 | 1.52 | 1.01 | 1.60 | 1.33 | 1.34 | 1.18 | 1.18 | 1.32 |
| Copper plate shear adhesion strength (a) | N/mm$^2$ | 13.4 | 12.4 | 14.6 | 16.2 | 11.7 | 12.5 | 14.2 | 10.6 | 11.3 | 11.4 | 11.3 |
| Copper plate shear adhesion strength (b) after heat cycle | N/mm$^2$ | 12.9 | 11.8 | 13.8 | 15.3 | 9.8 | 11.9 | 12.1 | 10.1 | 10.7 | 11.3 | 8.7 |
| Adhesion strength retention rate (b/a) |  | 0.96 | 0.95 | 0.95 | 0.94 | 0.84 | 0.95 | 0.85 | 0.95 | 0.95 | 0.99 | 0.77 |
| Gelling time (170° C.) | s | 424 | 358 | 330 | 310 | 361 | 363 | 407 | 421 | 346 | 283 | 295 |
| Water absorption rate | % | 2.40 | 2.43 | 2.42 | 2.53 | 2.55 | 2.79 | 2.89 | 3.01 | 3.13 | 2.89 | 3.02 |
| Impact test |  | ◎ | ◎ | Δ | ◎ | Δ | ○ | ◎ | ◎ | Δ | ◎ | ○ |

TABLE 4

|  |  |  | Comparative Example | | | | | |
|---|---|---|---|---|---|---|---|---|
|  |  |  | 3 | 4 | 5 | 6 | 7 | 8 |
| Composition | Epoxy resin composition A | parts by mass |  |  |  |  |  |  |
|  | Epoxy resin composition B |  |  |  |  |  |  |  |
|  | Epoxy resin composition C |  |  |  |  |  |  |  |
|  | Epoxy resin D |  |  |  |  |  |  |  |
|  | Epoxy resin composition E |  |  |  |  |  |  |  |
|  | Epoxy resin composition F |  |  |  |  |  |  |  |
|  | Epoxy resin composition G |  |  |  |  |  |  |  |
|  | Epoxy resin composition H |  |  |  |  |  |  |  |
|  | Epoxy resin composition I |  |  |  |  |  |  |  |
|  | Epoxy resin composition J |  |  |  |  |  |  |  |
|  | Epoxy resin composition K |  | 50 |  |  |  |  |  |
|  | Epolite 40E |  |  | 50 |  |  |  |  |
|  | YED216 |  |  |  | 50 |  |  |  |
|  | AER260 |  |  |  |  | 50 |  |  |
|  | AER6011 |  |  |  |  |  | 50 |  |
|  | YL983U |  | 50 | 50 | 50 | 50 | 50 | 100 |
|  | Diaminodiphenylmethane |  | 22.0 | 34.4 | 36.7 | 29.2 | 21.9 | 29.2 |
| Measurement results | Tg | ° C. | 142 | 52 | 67 | 163 | 143 | 158 |
|  | Storage modulus at 30° C. | MPa | 3432 | 1398 | 1512 | 3340 | 2760 | 4202 |
|  | Elastic modulus at (Tg − 20) ° C. | MPa | 2875 | 1380 | 673 | 2673 | 1024 | 3980 |
|  | Elastic modulus at (Tg + 20) ° C. | MPa | 110 | 263 | 102 | 47.2 | 36.6 | 49.7 |
|  | E'/(273 + Tg/3) |  | 10.7 | 4.8 | 5.1 | 10.2 | 8.6 | 12.9 |
|  | E'(Tg − 20)/E'(Tg + 20) |  | 26.1 | 5.2 | 6.6 | 56.6 | 28.0 | 80.1 |
|  | Bending strength | MPa | 452 | 367 | 353 | 423 | 382 | 340 |
|  | Fracture toughness ($K_{Ic}$) | MPa/m$^{0.5}$ | 0.98 | 1.25 | 1.18 | 0.68 | 0.85 | 0.63 |
|  | Copper plate shear adhesion strength (a) | N/mm$^2$ | 10.5 | 11.9 | 9.4 | 11.7 | 11.2 | 10.2 |
|  | Copper plate shear adhesion strength (b) after heat cycle | N/mm$^2$ | 9.6 | 7.8 | 6.3 | 11.2 | 8.9 | 9.6 |
|  | Adhesion strength retention rate (b/a) |  | 0.91 | 0.66 | 0.67 | 0.96 | 0.79 | 0.94 |
|  | Gelling time (170° C.) | s | 187 | 421 | 346 | 183 | 210 | 173 |
|  | Water absorption rate | % | 3.35 | 3.01 | 3.13 | 2.51 | 4.12 | 2.43 |
|  | Impact test |  | x | ○ | ○ | x | x | x |

TABLE 5

| | | | \multicolumn{10}{c}{Example} |
|---|---|---|---|---|---|---|---|---|---|---|---|---|
| | | | 22 | 23 | 24 | 25 | 26 | 27 | 28 | 29 | 30 | 31 |
| Epoxy resin | Epoxy resin composition A | parts by mass | 100 | | | | | | | | | |
| | Epoxy resin composition B | | | 100 | | | | | | | | |
| | Epoxy resin composition C | | | | 100 | | | | | | | |
| | Epoxy resin D | | | | | 100 | | | | | | |
| | Epoxy resin composition E | | | | | | 100 | | | | | |
| | Epoxy resin composition F | | | | | | | 100 | | | | |
| | Epoxy resin composition G | | | | | | | | 100 | | | |
| | Epoxy resin composition H | | | | | | | | | 100 | | |
| | Epoxy resin composition I | | | | | | | | | | 100 | |
| | Epoxy resin composition J | | | | | | | | | | | 100 |
| | Epoxy resin composition K | | | | | | | | | | | |
| | Epolite 40E | | | | | | | | | | | |
| | YED216 | | | | | | | | | | | |
| | AER260 | | | | | | | | | | | |
| | YL983U | | | | | | | | | | | |
| Curing agent | Ethacure 100 | | 13.3 | | | | 11.9 | | 10.3 | 15.7 | 14.6 | |
| | MEH8000H | | | 58.9 | 40.9 | 53.7 | | | | | | |
| | Rikacid MHT | | | | | | | 55.4 | | | | 48.5 |
| | HX3941 | | 5 | 5 | 5 | 5 | 5 | 5 | 5 | 5 | 5 | 5 |
| Filler | AC-5V | | 150 | 150 | 150 | 150 | 150 | 150 | 150 | 150 | 150 | 150 |
| Surface treatment agent | KBM-403 | | 1.4 | 1.4 | 1.4 | 1.4 | 1.4 | 1.4 | 1.4 | 1.4 | 1.4 | 1.4 |
| Evaluations | Melt viscosity at 25° C. | Pa·s | 25 | 50 | 47 | 52 | 38 | 30 | 45 | 28 | 110 | 42 |
| | Adhesion strength a to silver plating | N/mm$^2$ | 16.2 | 12.2 | 13.6 | 12.5 | 11.7 | 13.3 | 15.2 | 15.5 | 15.8 | 13.4 |
| | Adhesion strength b to silver plating after moisture absorption | N/mm$^2$ | 15.8 | 12.1 | 12.6 | 10.9 | 11.1 | 12.1 | 14.6 | 142 | 15.8 | 10.5 |
| | Adhesion strength retention rate (b/a) | | 0.98 | 0.99 | 0.93 | 0.87 | 0.95 | 0.91 | 0.96 | 0.92 | 1.00 | 0.78 |
| | Penetration test | | ◎ | ◎ | ◎ | ◎ | ○ | ◎ | ◎ | ◎ | ○ | ○ |
| | Drop test | | ◎ | Δ | ○ | Δ | ○ | ◎ | ◎ | ○ | ○ | ○ |
| | Reflow resistance | | ○ | ○ | ○ | ○ | ○ | ○ | ○ | ○ | ○ | ○ |
| | Thermal cycle resistance | | ◎ | ○ | ◎ | Δ | ○ | ◎ | ◎ | Δ | ○ | Δ |

TABLE 6

| | | | \multicolumn{5}{c}{Comparative Example} |
|---|---|---|---|---|---|---|---|
| | | | 9 | 10 | 11 | 12 | 13 |
| Epoxy resin | Epoxy resin composition A | parts by mass | | | | | |
| | Epoxy resin composition B | | | | | | |
| | Epoxy resin composition C | | | | | | |
| | Epoxy resin D | | | | | | |
| | Epoxy resin composition E | | | | | | |
| | Epoxy resin composition F | | | | | | |
| | Epoxy resin composition G | | | | | | |
| | Epoxy resin composition H | | | | | | |
| | Epoxy resin composition I | | | | | | |

TABLE 6-continued

| | | | Comparative Example | | | | |
|---|---|---|---|---|---|---|---|
| | | | 9 | 10 | 11 | 12 | 13 |
| | Epoxy resin composition J | | | | | | |
| | Epoxy resin composition K | | 100 | | | | |
| | Epolite 40E | | | 100 | | | |
| | YED216 | | | | 100 | | |
| | AER260 | | | | | 100 | |
| | YL983U | | | | | | 100 |
| Curing agent | Ethacure 100 | | | | | 25.1 | 27.5 |
| | MEH8000H | | | | | | |
| | Rikacid MHT | | 47.7 | 129.3 | 144.8 | | |
| | HX3941 | | 5 | 5 | 5 | 5 | 5 |
| Filler | AC-5V | | 150 | 150 | 150 | 150 | 150 |
| Surface treatment agent | KBM-403 | | 1.4 | 1.4 | 1.4 | 1.4 | 1.4 |
| Evaluations | Melt viscosity at 25° C. | Pa·s | 142 | 3.1 | 2.6 | 68 | 58 |
| | Adhesion strength a to silver plating | N/mm² | 12.4 | 12.6 | 13.2 | 15.5 | 15.3 |
| | Adhesion strength b to silver plating after moisture absorption | N/mm² | 12.2 | 8.7 | 92 | 10.8 | 11.5 |
| | Adhesion strength retention rate (b/a) | | 0.98 | 0.69 | 0.70 | 0.70 | 0.75 |
| | Penetration test | | x | x | x | ○ | ○ |
| | Drop test | | x | ○ | ○ | x | x |
| | Reflow resistance | | x | x | x | x | x |
| | Thermal cycle resistance | | ○ | x | x | Δ | Δ |

The present application is based on Japanese Patent Application (Patent Application No. 2012-170493) filed Jul. 31, 2012 at the Japan Patent Office and Japanese Patent Application (Patent Application No. 2012-184476) filed Aug. 23, 2012 at the Japan Patent Office, the contents of which are incorporated herein by reference.

INDUSTRIAL APPLICABILITY

The epoxy resin composition and the epoxy resin of the present invention can be suitably used for sealants, adhesives, printed substrate materials, coating materials, composite materials, semiconductor sealants such as underfill and molding, electrically conductive adhesives such as ACF, printed wiring boards such as solder resist and cover lay film, and the like.

REFERENCE SIGNS LIST

1 . . . Semiconductor device, 2 . . . Substrate, 3 . . . Semiconductor chip, 4 . . . Solder bump, 5 . . . Circuit protection film, 6 . . . Solder resist, 7 . . . Sealing epoxy resin composition

The invention claimed is:

1. An epoxy resin composition comprising:
an epoxy resin represented by the following formula (1); and
an epoxy resin represented by the following formula (2):

[Formula 1]

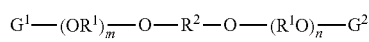
(1)

[Formula 2]

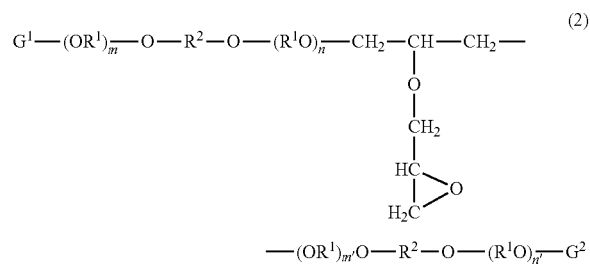
(2)

wherein m, n, m' and n' are each independently an integer of 1 to 30, $R^1$ and $R^2$ are each independently a divalent aliphatic group having 1 to 12 carbon atoms, or a divalent aromatic group having 6 to 40 carbon atoms, at least one of $R^1$ and $R^2$ represents a divalent aromatic group having 6 to 30 carbon atoms, $G^1$ represents a glycidyl group, and $G^2$ represents a hydrogen atom or a glycidyl group.

2. The epoxy resin composition according to claim 1, comprising:
100 parts by mass of the epoxy resin represented by formula (1); and
0.1 to 10 parts by mass of the epoxy resin represented by formula (2).

3. The epoxy resin composition according to claim 1, wherein $R^2$ in the formula (1) is any one selected from the group consisting of a phenylene group, a naphthylene group, a biphenylene group and a divalent aromatic group having structure represented by the following formula (3a):

[Formula 3]

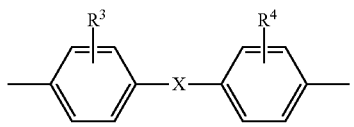

(3a)

wherein $R^3$ and $R^4$ each independently represent any one selected from the group consisting of a hydrogen atom, a halogen atom, a hydroxyl group, an alkoxy group having 1 to 12 carbon atoms, a carboxyl group and an alkyl group having 1 to 12 carbon atoms, and X represents any one selected from the group consisting of an alkylene group having 1 to 10 carbon atoms, —O—, —CO—, —COO—, —S—, —SO—, —SO$_2$— and —S—S—.

4. The epoxy resin composition according to claim 1, wherein at least one of $R^2$ in the formula (2) is any one selected from the group consisting of a phenylene group, a naphthylene group, a biphenylene group and a divalent aromatic group having the structure represented by the following formula (3b):

[Formula 4]

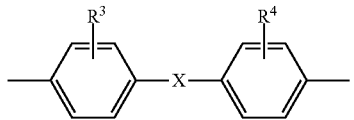

(3b)

wherein $R^3$ and $R^4$ each independently represent any one selected from the group consisting of a hydrogen atom, a halogen atom, a hydroxyl group, an alkoxy group having 1 to 12 carbon atoms, a carboxyl group and an alkyl group having 1 to 12 carbon atoms, and X represents any one selected from the group consisting of an alkylene group having 1 to 10 carbon atoms, —O—, —CO—, —COO—, —S—, —SO—, —SO$_2$— and —S—S—.

5. The epoxy resin composition according to claim 1, wherein the formula (1) is represented by the following formula (4), and the formula (2) is represented by the following formula (5):

[Formula 5]

(4)

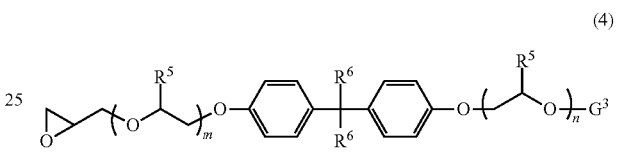

wherein $R^5$ and $R^6$ each independently represent a hydrogen atom or a methyl group, $G^3$ represents a hydrogen atom or a glycidyl group, and m and n are each independently an integer of 1 or more and satisfy a relation represented by $3 \leq (m+n) \leq 12$,

[Formula 6]

(5)

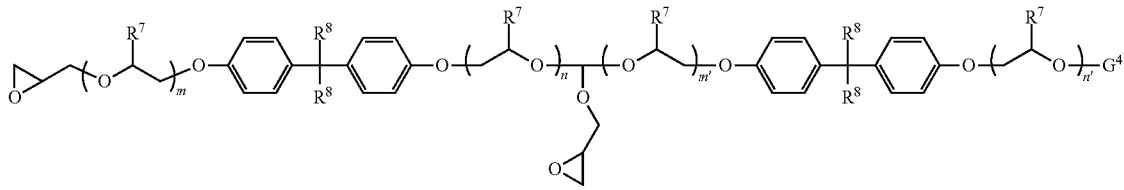

wherein $R^7$ and $R^8$ each independently represent a hydrogen atom or a methyl group, and $G^4$ represents a hydrogen atom or a glycidyl group; and m, n, m' and n' are each independently an integer of 1 or more, and satisfy a relation represented by $6 \leq (m+n+m'+n') \leq 20$.

6. The epoxy resin composition according to claim 5, wherein $G^4$ in the formula (5) is a glycidyl group.

7. An epoxy resin composition comprising:
the epoxy resin composition according to claim 1; and
a curing agent.

8. A cured product obtained by curing the epoxy resin composition according to claim 7.

9. An electronic part comprising the cured product according to claim 8.

* * * * *